(12) United States Patent
Barber

(10) Patent No.: US 11,629,346 B2
(45) Date of Patent: Apr. 18, 2023

(54) STING-DEPENDENT ACTIVATORS FOR TREATMENT OF DISEASE

(71) Applicant: UNIVERSITY OF MIAMI, Miami, FL (US)

(72) Inventor: Glen N. Barber, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 204 days.

(21) Appl. No.: 16/621,820

(22) PCT Filed: Jun. 12, 2018

(86) PCT No.: PCT/US2018/036997
§ 371 (c)(1),
(2) Date: Dec. 12, 2019

(87) PCT Pub. No.: WO2018/231752
PCT Pub. Date: Dec. 20, 2018

(65) Prior Publication Data
US 2021/0355490 A1    Nov. 18, 2021

Related U.S. Application Data

(60) Provisional application No. 62/518,292, filed on Jun. 12, 2017.

(51) Int. Cl.
*C07H 21/04* (2006.01)
*C12N 15/113* (2010.01)
*A61K 39/00* (2006.01)
*C12N 15/86* (2006.01)

(52) U.S. Cl.
CPC ........ *C12N 15/113* (2013.01); *A61K 39/0011* (2013.01); *C12N 15/86* (2013.01); *A61K 2039/53* (2013.01); *A61K 2039/54* (2013.01); *C12N 2310/17* (2013.01); *C12N 2310/315* (2013.01); *C12N 2320/30* (2013.01)

(58) Field of Classification Search
None
See application file for complete search history.

(56) References Cited

PUBLICATIONS

Ishikawa et al. (Nature, 2009, 461:788-792).*
Li et al. ("Regulating STING in health and disease." Journal of Inflammation 14.1 (2017): 1-21).*

* cited by examiner

*Primary Examiner* — Kimberly Chong
(74) *Attorney, Agent, or Firm* — Sci-Law Strategies, PC

(57) ABSTRACT

The present disclosure relates, in general, to oligonucleotides that stimulate STING (STimulator of INterferon Genes) activity and increase activity of immune cells. The disclosed STING activators (STAVs) are useful in the treatment of cancer and other immune-mediated conditions.

21 Claims, 14 Drawing Sheets
Specification includes a Sequence Listing.

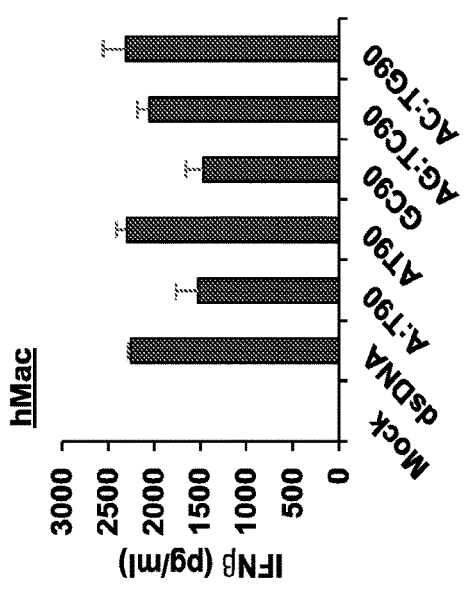
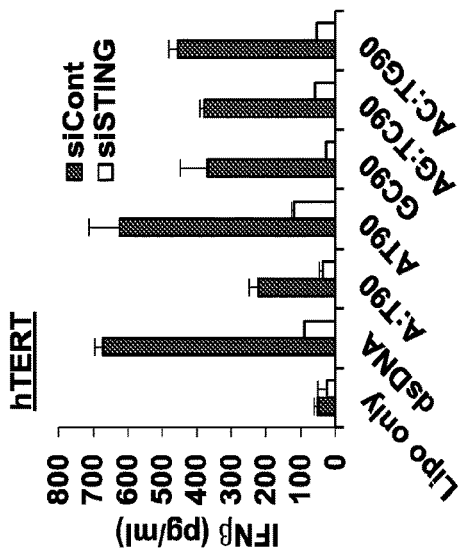
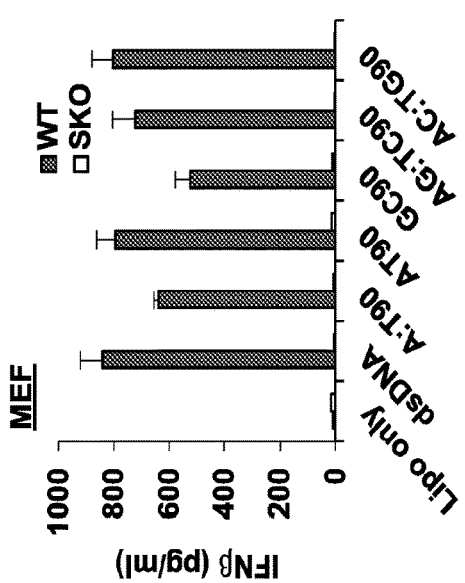
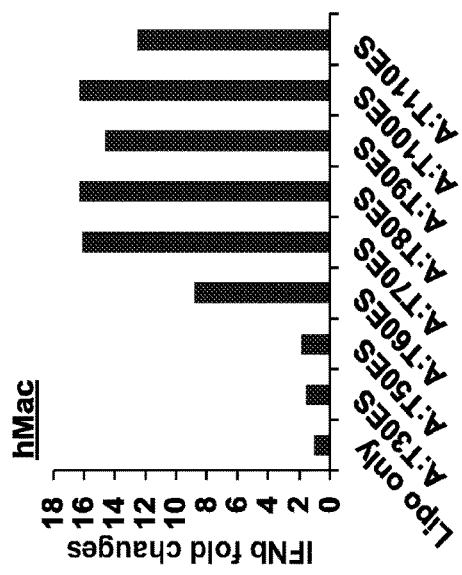
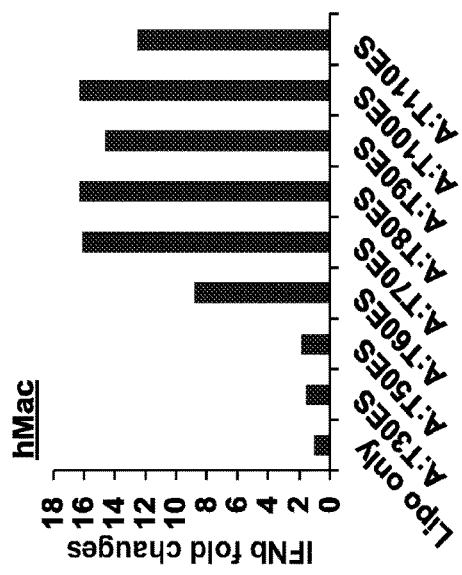
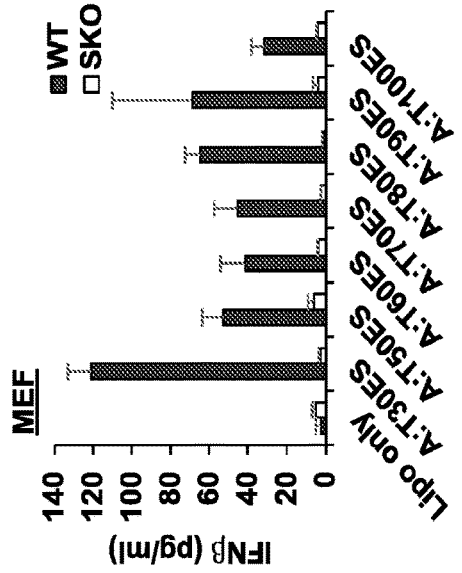

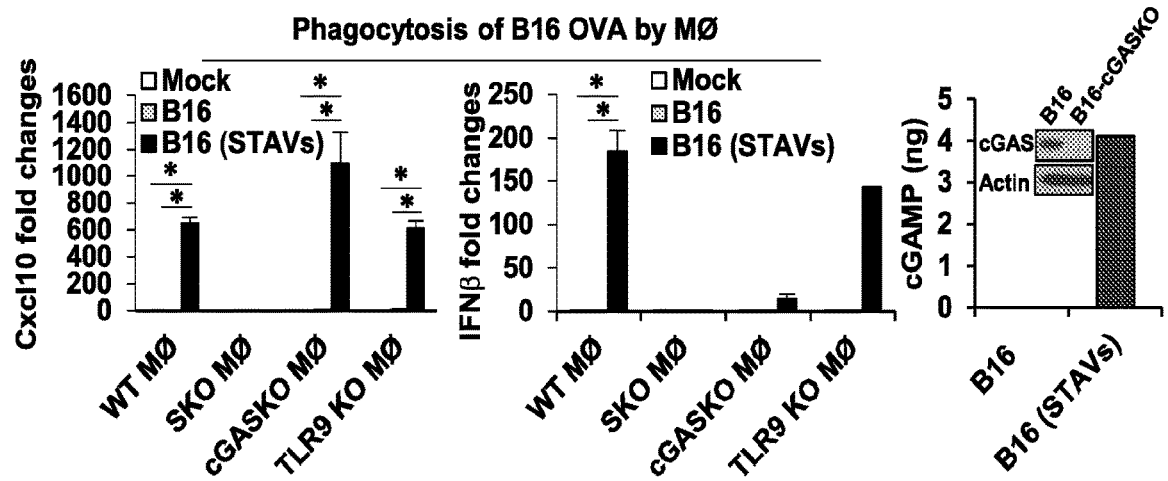
Fig. 6A
Fig. 6B
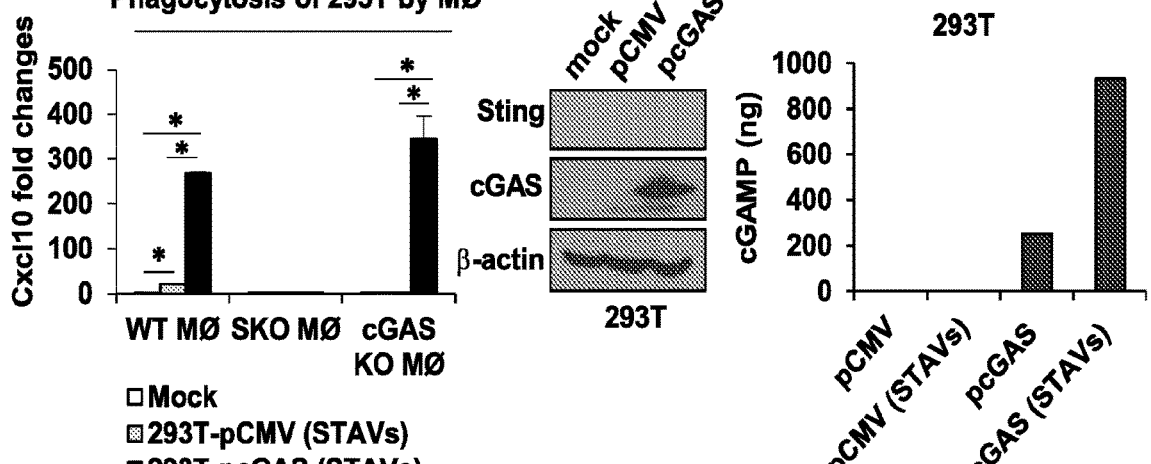
Fig. 6C
Fig. 6D
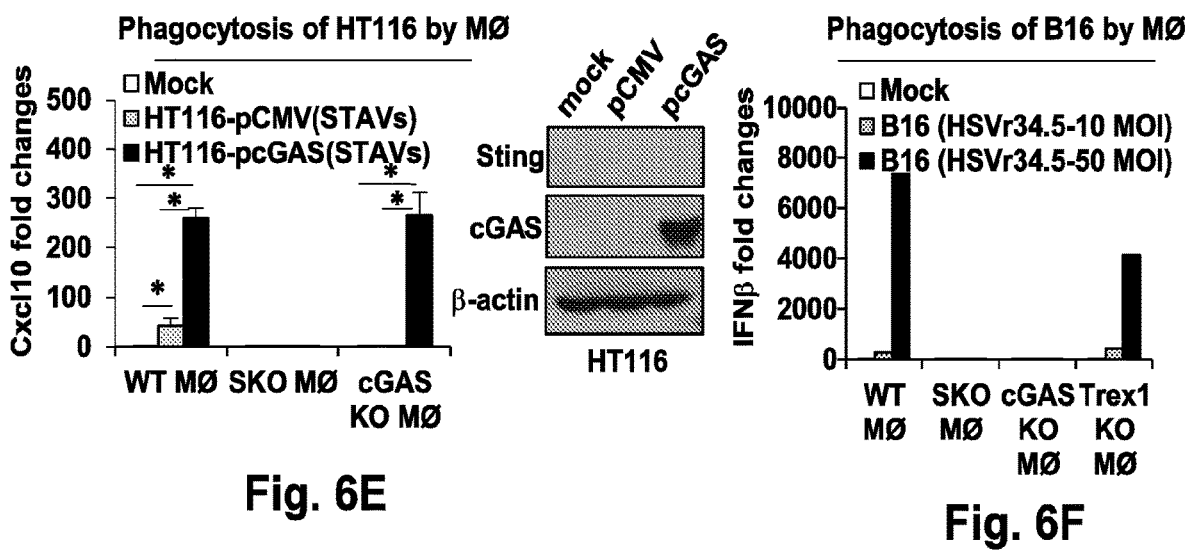
Fig. 6E
Fig. 6F

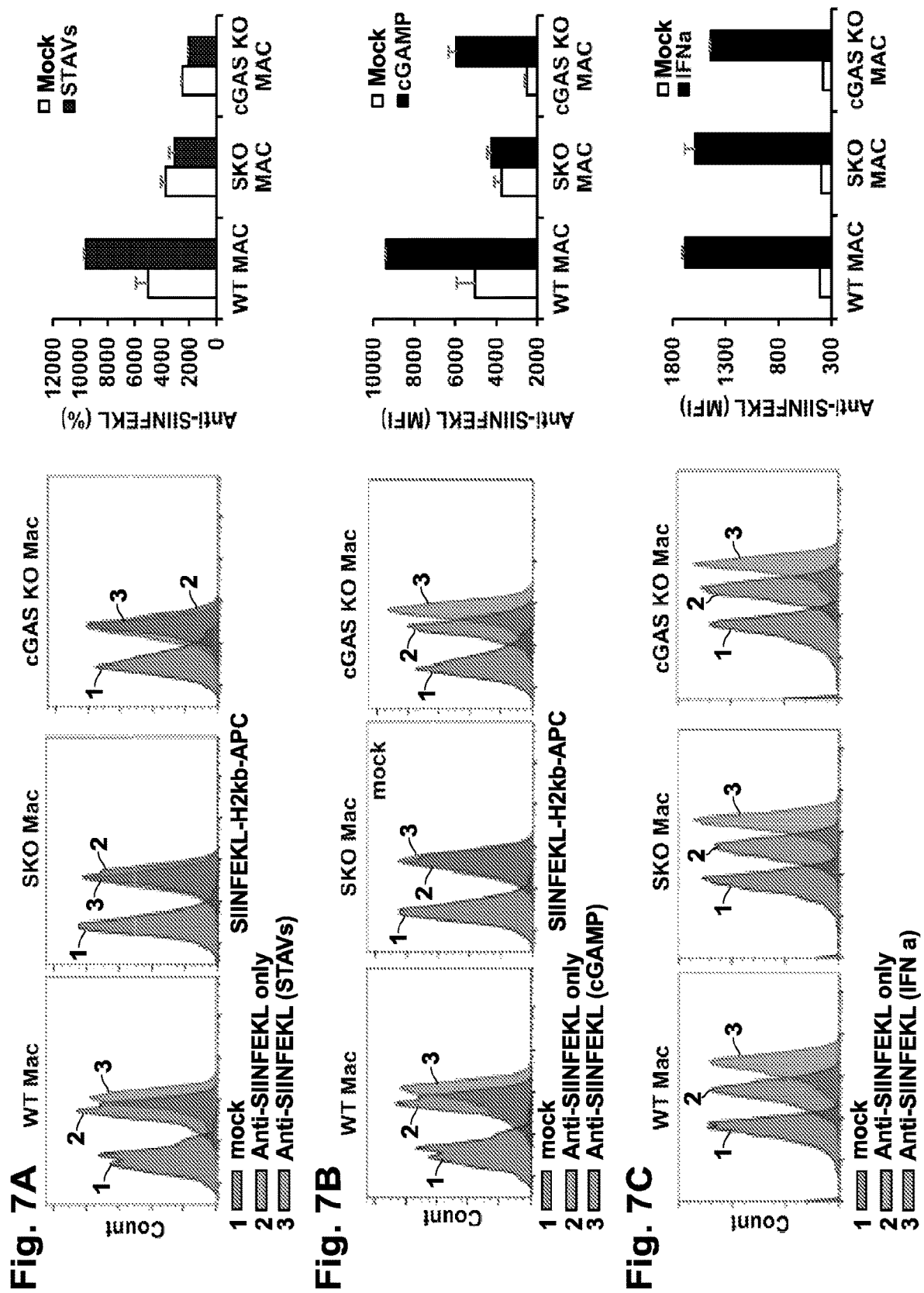

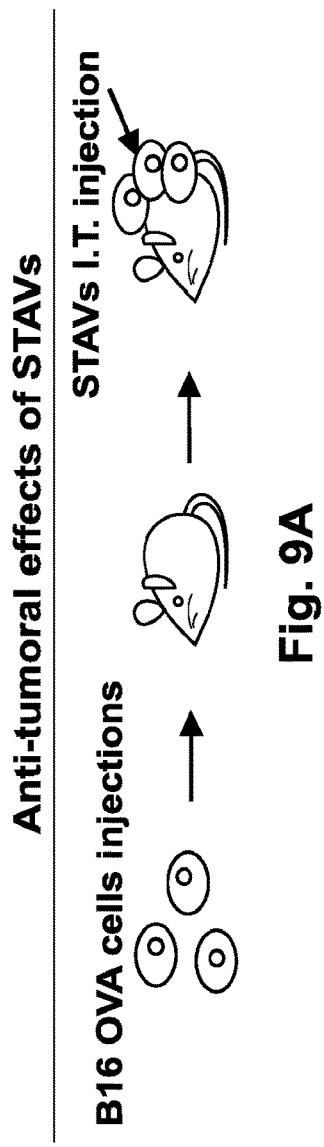
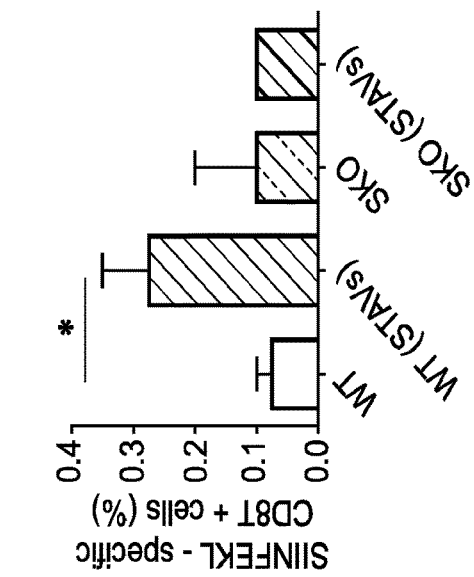
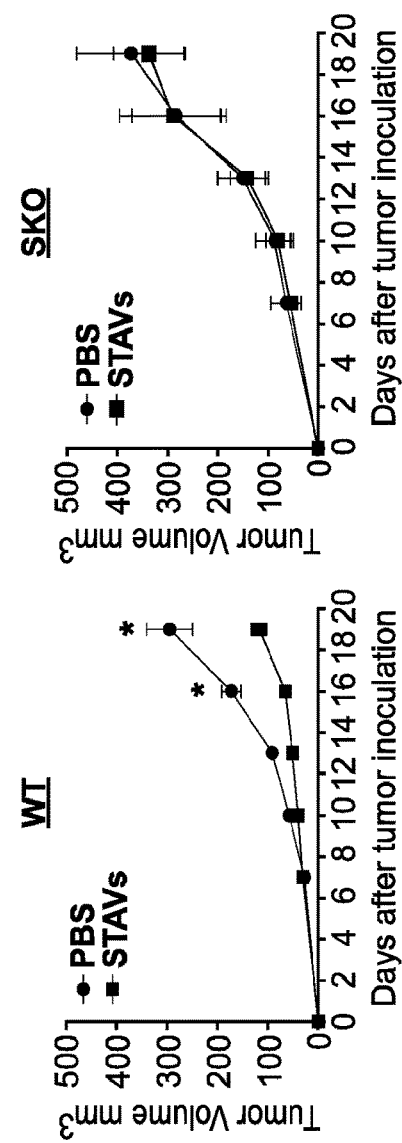
Fig. 9A
Fig. 9B
Fig. 9C
Fig. 9D

Dead cell vaccinations
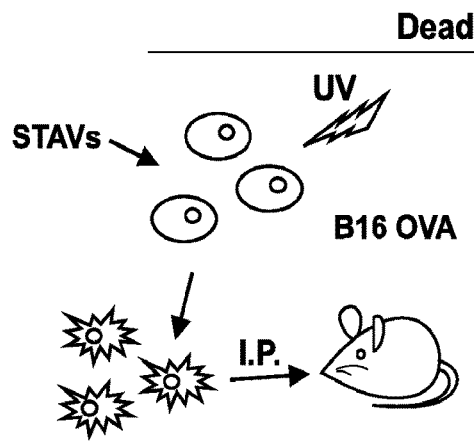
Fig. 10A
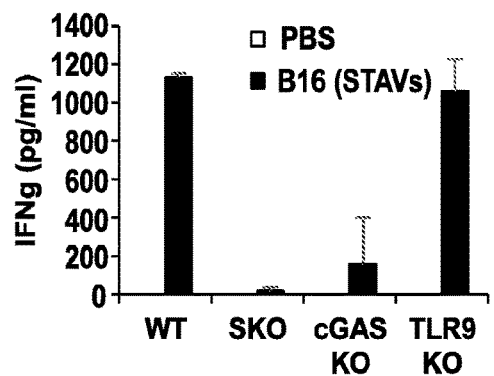
Fig. 10B
Anti-metastatic effects of STAVs
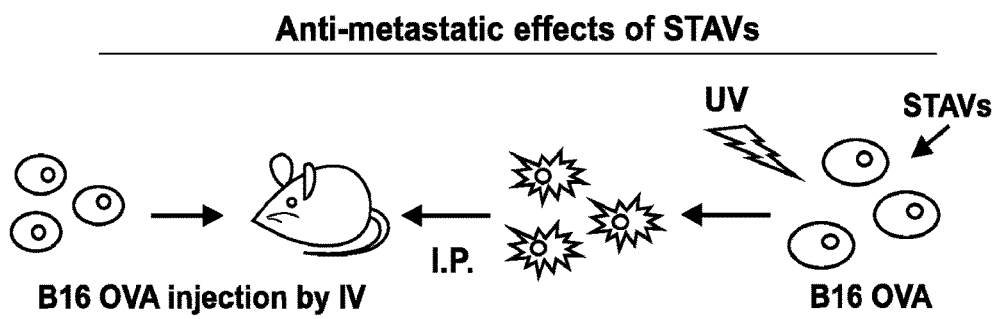
Fig. 10C
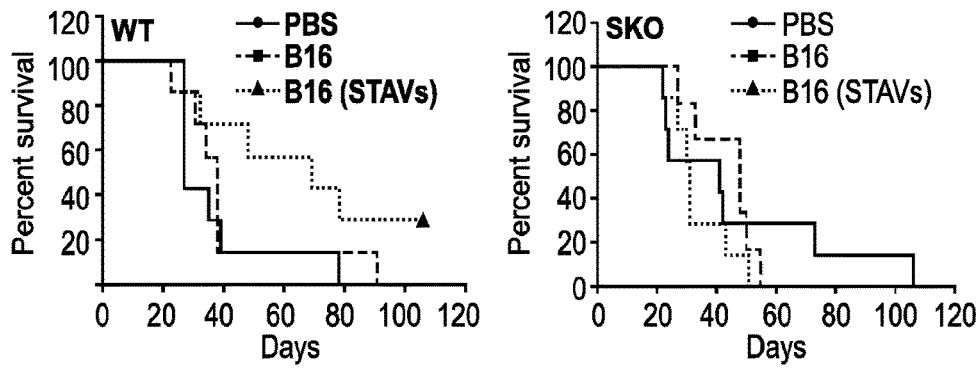
Fig. 10D              Fig. 10E
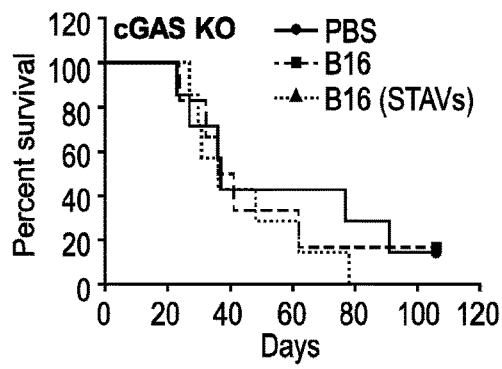          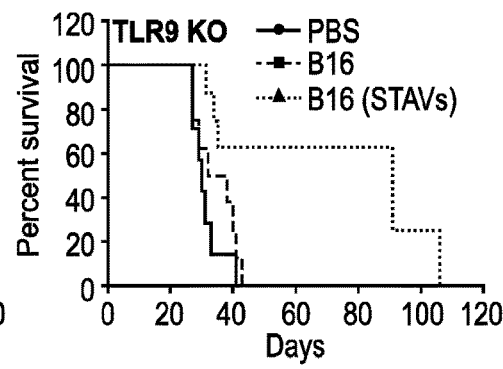
Fig. 10F              Fig. 10G

| Gene Symbol | STAVs vs Nock |
|---|---|
| Ccl5 | 80.0 |
| Ifit1 | 66.1 |
| Ifih1 | 49.9 |
| Cxcl10 | 34.5 |
| Mx2 | 21.3 |
| Gbp7 | 20.3 |
| Rsad2 | 19.0 |
| Isg15 | 17.9 |
| Gbp3 | 14.1 |
| Gm20559 | 13.4 |
| Parp14 | 12.4 |
| Ddx58 | 11.2 |
| 1700007K13Rik | 9.1 |
| Trp53inp1 | 8.7 |
| Klhl38 | 8.0 |
| Oasl1 | 7.7 |
| Tmem140 | 7.6 |
| Gbp2 | 7.1 |
| Mx1 | 6.8 |
| Usp18 | 6.8 |
| Parp9 | 6.3 |
| NA | 6.3 |
| Oasl2 | 6.1 |
| Btg2 | 5.9 |
| Plk2 | 5.8 |
| Apol9b | 5.7 |
| Cmpk2 | 5.6 |
| Irgm1 | 5.5 |
| Csf1 | 5.0 |
| 9230114K14Rik | 4.9 |
| Ddx60 | 4.7 |
| NA | 4.7 |
| Tapbp | 4.6 |
| Irgm2 | 4.4 |
| Samd9l | 4.4 |
| Herc6 | 4.4 |
| NA | 4.4 |
| Apobec1 | 4.3 |
| Sesn2 | 4.2 |
| Ifitm3 | 4.1 |
| Tnfrsf10b | 4.1 |
| Stat2 | 4.0 |
| Rhbdf2 | 3.9 |
| Nfkbie | 3.9 |
| Trim21 | 3.8 |
| NA | 3.7 |
| Znfx1 | 3.7 |
| Xaf1 | 3.6 |

Fig. 11

| Gene Symbol | WT MØ (293) | WT MØ (293-STAVs) | SKO MØ (293) | SKO MØ (293-STAVs) |
|---|---|---|---|---|
| Gm14446 | 2.7 | 86.4 | 1.1 | 1.0 |
| Cmpk2 | 5.2 | 80.0 | 1.7 | 1.5 |
| Cxcl10 | 3.1 | 64.1 | 1.4 | 1.4 |
| NA | 4.4 | 56.3 | 16.3 | 10.7 |
| Gm4951 | 3.1 | 51.8 | 1.0 | 1.1 |
| NA | 1.1 | 51.1 | 34.6 | 32.5 |
| Ccl12 | 2.2 | 45.4 | 2.6 | 1.6 |
| Rsad2 | 4.2 | 44.8 | 1.3 | 1.2 |
| Ifi205 | 3.9 | 43.7 | 1.1 | 1.0 |
| Cd69 | 1.8 | 42.0 | 1.1 | 1.2 |
| Ifit1 | 3.5 | 40.2 | 1.2 | 0.9 |
| Iigp1 | 1.4 | 35.4 | 0.5 | 0.6 |
| Igtp | 2.8 | 33.6 | 1.8 | 1.5 |
| Usp18 | 3.4 | 31.4 | 1.5 | 1.0 |
| Pyhin1 | 0.9 | 31.2 | 0.4 | 0.3 |
| Mx1 | 1.7 | 29.3 | 0.6 | 0.6 |
| Mx2 | 2.1 | 27.7 | 0.7 | 0.7 |
| Gbp5 | 1.3 | 27.2 | 0.9 | 0.7 |
| NA | 1.7 | 24.6 | 1.1 | 0.9 |
| Pydc3 | 4.0 | 24.2 | 1.0 | 0.7 |
| Oasl1 | 1.9 | 24.0 | 1.2 | 1.2 |
| Tnfsf10 | 1.5 | 23.2 | 0.9 | 0.8 |
| Serpinb2 | 23.0 | 23.2 | 19.5 | 19.0 |
| Trim30c | 1.1 | 20.5 | 0.9 | 0.7 |
| NA | 3.6 | 20.1 | 2.7 | 2.4 |
| Gbp3 | 1.6 | 19.4 | 1.1 | 1.2 |
| NA | 10.1 | 19.1 | 9.4 | 9.6 |
| Pydc4 | 0.8 | 18.9 | 0.3 | 0.3 |
| NA | 9.5 | 18.9 | 2.7 | 6.0 |
| Ifit2 | 1.7 | 18.2 | 1.2 | 1.0 |
| NA | 14.5 | 18.1 | 6.1 | 6.1 |
| NA | 14.5 | 18.1 | 6.1 | 6.1 |
| Gm12250 | 0.9 | 17.4 | 0.5 | 0.5 |
| Irf7 | 1.4 | 16.9 | 1.0 | 0.8 |
| NA | 1.4 | 16.3 | 0.9 | 0.9 |
| NA | 1.1 | 16.2 | 0.9 | 0.6 |
| NA | 5.6 | 15.9 | 3.4 | 1.6 |
| Isg15 | 1.9 | 15.7 | 1.0 | 0.7 |
| Phf11b | 1.1 | 15.7 | 0.9 | 0.9 |
| Ccl2 | 5.6 | 14.9 | 5.4 | 5.9 |
| NA | 4.7 | 14.6 | 14.0 | 20.7 |
| Ddx60 | 0.9 | 14.5 | 1.1 | 0.9 |
| Zbp1 | 1.7 | 13.8 | 1.1 | 1.1 |
| NA | 1.1 | 13.5 | 0.5 | 0.5 |
| Cd274 | 3.1 | 13.1 | 2.5 | 3.6 |

Fig. 12

STING-DEPENDENT ACTIVATORS FOR TREATMENT OF DISEASE

CROSS-REFERENCE TO RELATED APPLICATIONS

This application claims priority to U.S. Provisional Patent Application No. 62/518,292 filed on Jun. 12, 2017, the disclosure of which is hereby incorporated by reference in its entirety.

INCORPORATION BY REFERENCE OF MATERIALS SUBMITTED ELECTRONICALLY

This application contains, as a separate part of the disclosure, a sequence listing in computer readable form (Filename: 50648A_Seqlisting.txt; Size: 4,094 Bytes; Created: Jun. 11, 2018), which is incorporated by reference in its entirety.

FIELD OF THE INVENTION

The present disclosure relates, in general, to oligonucleotides that stimulate STING (STimulator of INterferon Genes) activity and increase activity of immune cells. The disclosed STING activators (STAVs) are useful in the treatment of cancer and other immune-mediated conditions.

BACKGROUND

Cellular host defense responses to pathogen invasion principally involves the detection of pathogen associated molecular patterns (PAMPs) such as viral nucleic acid or bacterial cell wall components including lipopolysaccharide or flagellar proteins that results in the induction of antipathogen genes. For example, viral RNA can be detected by membrane bound Toll-like receptors (TLR's) (e.g. TLR 3 and 7/8) or by TLR-independent intracellular DExD/H box RNA helicases referred to as retinoic acid inducible gene 1 (RIG-I) or melanoma differentiation associated antigen 5 (MDAS, also referred to as IFIH1 and helicard). These events culminate in the activation of downstream signaling events, much of which remains unknown, leading to the transcription of NF-κB and IRF3/7-dependent genes, including type I IFN.

The generation of T cells that recognize specific antigens presented on tumor cells constitutes an important host defense response that has evolved to eliminate the development of cancer (1). The mechanisms underlining the stimulation of antigen presenting cells (APC) and the priming of tumor specific T cells remains to be clarified but is thought to involve the generation of immunostimulatory type I interferon (IFN) and other cytokines triggered by DNA from the engulfed cell (2-6). The innate immune pathways governing these events involve STING (stimulator of interferon genes) signaling within phagocytes such as CD8+ dendritic cells (7-10). STING recognizes cyclic dinucleotides including c-di-GMP or c-di-AMP secreted by intracellular bacteria or cyclic-GMP-AMP (cGAMP) generated by the cellular synthase Cyclic GMP-AMP synthase (cGAS) following association with cytosolic dsDNA species (11, 12). Generally, non-tumorigenic cells undergoing apoptosis avoid activating APC's, an event that would otherwise cause lethal autoinflammatory disease due to chronic cytokine production (13-15), by likely adopting comparable processes, tumor cells are also able to avoid the activation of APC's and thus the subsequent spontaneous generation of T-cells. In contrast, microbial infected cells are potently able to activate APCs following engulfment, and can robustly generate anti-pathogen T-cells (16, 17). While DNA from engulfed cells is known to play a key role in stimulating APC's (18), how phagocytes differentiate between an apoptotic/tumorigenic cell and an infected cell, both of which harbor considerable amounts of cellular DNA, remains to be fully determined.

SUMMARY OF THE DISCLOSURE

The present disclosure demonstrates that dsDNA having a structure sufficient to stimulate an immune response is useful to activate STING (STimulator of INterferon Genes) and has an effect at stimulating immune response in vivo, suggesting the STING activators will be useful in the treatment of autoimmune disease, infection and cancer.

The disclosure provides an activator of STING (STimulator of INterferon Genes) comprising a double stranded DNA (dsDNA) having a modified 5' end and comprising between 25 and 90 nucleotides, wherein the activator induces STING signaling.

In various embodiments, the dsDNA is approximately 30 nucleotides in length. In various embodiments the dsDNA is approximately 70 nucleotides in length. It is contemplated that the STING activator dsDNA can be 20, 25, 30, 35, 40, 45, 50, 55, 60, 65, 70, 75, 80, 85 or 90 nucleotides in length.

In various embodiments, the dsDNA is AT rich or GC rich. In various embodiments, the activator sequence may consist of all A residues, all T residues, alternating A and T residues, or a mixture of A and T residues, e.g., wherein 20, 30, 40, 50, 60, 70, 80 or 90% or more of the nucleotides are A residues or T residues, and the remaining residues are the complementary nucleotide. It is also contemplated that the activator sequence may consist of all G residues, all C residues, alternating G and C residues, or a mixture of G and C residues, e.g., wherein 20, 30, 40, 50, 60, 70, 80 or 90% or more of the nucleotides are G residues or C residues, and the remaining residues are the complementary nucleotide. Further, the activator polynucleotide may be a mixture of A, T, G and C nucleotides.

In various embodiments, the 5' end and/or the 3' end of the activator polynucleotide is modified. In some embodiments, the 5' end is modified by phosphorothioate linkage. In some embodiments, the 3' end is modified by phosphorothioate linkage. In some embodiments, the first three nucleotides at the 5' end are modified by phosphorothioate linkage. In some embodiments, the last three nucleotides at the 3' end are modified by phosphorothioate linkage. In various embodiments, the activator nucleotide is modified every 2, 3, 4, or 5 nucleotides. In various embodiments, the activator nucleotide is modified at every third base.

In various embodiments, the activator has a sequence as follows: Sense strand: AAAAAAAAAAAAAAAAAAA-AAAAAAAAAAAAAAAAAAAAAAAAAAAAAA-AAAA AAAAAAAAAAAAAAAAAAAAAAAAAA-AAAAAAAA (SEQ ID NO: 1), optionally wherein the first three and last three nucleotides are modified by phosphorothioate linkage;

Anti-Sense strand: TTTTTTTTTTTTTTTTTTTTTT-TTTTTTTTTTTTTTTTTTTTTTTTTTTTTTTTTTTT-TTT TTTTTTTTTTTTTTTTTTTTTTT (SEQ ID NO: 2), optionally wherein the first three and last three nucleotides are modified by phosphorothioate linkage.

Also contemplated by the disclosure is a composition comprising a STING activator as described herein and a pharmaceutically acceptable carrier. In various embodiments, the composition is a sterile composition.

Further provided by the disclosure is a vector comprising a STING activator as described herein comprising a double stranded DNA (dsDNA) having a modified 5' end and comprising between 25 and 90 nucleotides, wherein the activator induces STING signaling.

Also provided is a vaccine comprising a STING activator as described herein comprising a double stranded DNA (dsDNA) having a modified 5' end and comprising between 25 and 90 nucleotides, wherein the activator induces STING signaling.

In various embodiments, the nucleotide is in a vector. In various embodiments, the vector is a viral or a plasmid vector. In one embodiment, the viral vector is selected from the group consisting of vesicular stomatitis virus (VSV), a lentivirus, an acdenovirus, an adeno-associated virus, a vaccinia virus and a modified vaccinia Ankara (MVA) virus.

The disclosure also contemplates a method of activating STING in a subject in need thereof comprising administering a composition comprising an activator of STING (STimulator of INterferon Genes) described herein comprising a double stranded DNA (dsDNA) having a modified 5' end and comprising between 25 and 90 nucleotides, wherein the activator induces STING signaling.

Provided herein is a method of stimulating an immune response in a subject in need thereof comprising administering a composition comprising an activator of STING (STimulator of INterferon Genes) as described herein comprising a double stranded DNA (dsDNA) having a modified 5' end and comprising between 25 and 90 nucleotides, wherein the activator induces STING signaling.

In various embodiments, the subject is suffering from cancer or a microbial infection. Exemplary cancers and microbial infections contemplated herein are described further in the Detailed Description.

The disclosure contemplates a method of decreasing the size of a tumor in a subject comprising administering a composition comprising an activator of STING (STimulator of INterferon Genes) comprising a double stranded DNA (dsDNA) having a modified 5' end and comprising between 25 and 90 nucleotides, wherein the activator induces STING signaling.

Also provided is a method of treating cancer in a subject comprising administering a composition comprising an activator of STING (STimulator of INterferon Genes) comprising a double stranded DNA (dsDNA) having a modified 5' end and comprising between 25 and 90 nucleotides, wherein the activator induces STING signaling.

In various embodiments, the cancer is ovarian cancer, colon cancer, melanoma, breast cancer or lung cancer.

In various embodiments, tumor size in the subject is decreased by about 25-50%, about 40-70% or about 50-90% or more.

In various embodiments, the STING activator is administered intratumorally, intravenously, intra-arterially, intraperitoneally, intranasally, intramuscularly, intradermally or subcutaneously.

In various embodiments, the STING activator induces infiltration of immune cells into the tumor. In various embodiments, the immune cells are macrophages or other phagocytes.

In various embodiments, the STING activator oligonucleotide remains cytosolic in a cell. In various embodiments, the STING activator induces Cxcl10 and/or type I IFN cytokine production.

BRIEF DESCRIPTION OF THE DRAWINGS

FIG. 1A-1J. Various STING ligands with different sequences and polynucleotide length. (FIG. 1A-1C): different sequence, (FIG. 1D-1F): different length of AT rich ligands, (FIG. 1G-I): different length of GC rich ligands (FIG. 1G-1I). IFNb ELISA assay of MEFs (FIG. 1A, 1D, 1G) and hTERT (FIG. 1B, 1E, 1H). IFNb ELISA assay (FIG. 1C) and qPCR of IFNb (FIG. 1F-1I) in primary human macrophages treated with 3 ug/ml of STING ligands. (FIG. 1J) Evaluation of DNA amount in B16 OVA cells transfected with 3 ug of STAV.

(FIG. 2A) Confocal analysis and flow cytometry analysis of B16 OVA cells (B16) transfected with FAM labeled STAVs (green). DAPI (blue) and anti-Calreticulin (red) as counter staining. (FIG. 2B) Gene array analysis of B16 cells transfected with STAVs. Highest variable inflammation-related genes are shown. (FIG. 2C) qPCR analysis of Ifnβ, Cxcl10 and Ifit3 in B16 OVA cells same as in (FIG. 2B). (FIG. 2D) Western blot analysis of STING, p65 and IRF3 in B16 cells transfected with STAVs at following time points. (FIG. 2E) Immunofluorescent analysis using anti-STING and anti-p65 in B16 cells at 3 hours after transfection of STAVs. (FIG. 2F) Schematic representation of the phagocytosis of B16 cells by macrophages. B16 cells were transfected by STAVs for 3 hours and irradiated by UV (120 mJ/cm). The irradiated B16 cells were feed to macrophages (MØ) at 24 hours after UV irradiation. (FIG. 2G) Confocal analysis and (FIG. 2H) Flow cytometry analysis in macrophages following cellular engulfment of B16 cells transfected with FAM labeled STAVs. qPCR analysis of Cxcl10 (FIG. 2I) and IFNβ (FIG. 2J) in wild type (WT) and sting knock out (SKO) macrophages (WT MØ and SKO MØ) following engulfment of B16 cells with/without STAVs. Flow cytometry for CD86 (FIG. 2K) and H2Kb (FIG. 2L) on macrophages following phagocytosis of B16 cells. Data is representative of at least three independent experiments. Error bars indicate s.d. *; p<0.05, Student's t-test.

(FIG. 3A) Flow cytometry analysis of B16 OVA cells stained with propidium iodide and annexin V. (FIG. 3B) Flow cytometry analysis for residual FITC-labelled DNA in B16 OVA cells following UV irradiation. (FIG. 3c) Western blot analysis using anti-OVA in B16 OVA cells following UV irradiation. Beta actin was used as control. (FIG. 3D) Flow cytometry analysis in macrophages following cellular engulfment of CFSE labelled B16 OVA cells.

(FIG. 4A) Flow cytometry analysis in macrophages following cellular engulfment of HEK293 cells (293) transfected with FAM labeled STAVs. (FIG. 4B) Gene array analysis of WT and SKO macrophages following engulfment of irradiated 293 cells with/without STAVs. Highest variable inflammation-related genes are shown. qPCR analysis of Cxcl10 (FIG. 4C) and IFNβ (FIG. 4D) in same as in (FIG. 4A). Data is representative of at least three independent experiments. Error bars indicate s.d. *; p<0.05, Student's t-test.

(FIG. 5A) Western blot analysis of STING and cGAS in mouse embryonic fibroblasts (MEFs). (FIG. 5B) ELISA of IFNβ in WT, SKO and cGAS knock out (cGAS KO) transfected with STAVs. (FIG. 5C) Schematic representation of the phagocytosis of MEFs by macrophages. qPCR analysis of Cxcl10 (FIG. 5D) and IFNβ (FIG. 5E) in WT and SKO macrophages following engulfment of UV irradiated WT, SKO and cGAS KO MEFs with STAVs. (FIG. 5F) ELISA of IFNβ in 293T and hTERT cells transfected with STAVs. qPCR analysis of Cxcl10 (FIG. 5G) and IFNβ (FIG. 5H) in WT and SKO macrophages following engulfment of UV irradiated 293T cells with or without STAVs. Data is representative of at least three independent experiments. Error bars indicate s.d. *; p<0.05, Student's t-test.

FIG. 6A-6F. Extrinsic activation of the cGAS/STING axis in macrophages. (FIG. 6A) qPCR analysis of Cxcl10 and IFNβ in WT, SKO, cGAS KO and TLR9 KO macrophages following engulfment of STAVs treated B16 cells. (FIG. 6B) cGAS expression by Western blot and cGAMP amount by a hybrid mass spectrometer. (FIG. 6C) qPCR analysis of Cxcl10 in WT, SKO, and cGAS KO macrophages following engulfment of 293T cells containing STAVs. The 293T cells were reconstituted with pcGAS or pCMV as control vector. (FIG. 6D) Measurement of cGAMP levels by a hybrid mass spectrometer in 293T cells same as in (C). (FIG. 6E) qPCR analysis of Cxcl10 in WT, SKO, and cGAS KO macrophages following engulfment of HT116 cells containing STAVs. The HT116 cells were reconstituted with pcGAS or pCMV as control vector. (FIG. 6F) qPCR analysis of IFNβ in WT, SKO, cGAS KO, and Trex1 KO macrophages following engulfment of B16 cells infected with HSVγ34.5. The HT116 cells were reconstituted with pcGAS or pCMV as control vector. Error bars indicate s.d. *; p<0.05, Student's t-test.

FIG. 7A-7C. Activation of antigen presenting cells by STAVs. WT, SKO, cGAS KO macrophages were transfected with 3 ug/ml of (FIG. 7A) AT90ES or (FIG. 7B) cGAMP and (FIG. 7C) Ifnb treatment for 24 hours followed by pulsing with or without SIINFEKL. Antigen presentation was evaluated by flow cytometry analysis using antibody reacting with OVA peptide SIINFEKL bound to H-2Kb of MHC class I.

(FIG. 8A) Schematic representation of the phagocytosis of B16 cells by DNase I, DNase II, or Trex1 Knockout macrophages. B16 cells were transfected by STAVs for 3 hours and irradiated by UV (120 mJ/cm). The irradiated B16 cells were feed to three different genotypes of macrophages (MØ) at 24 hours after UV irradiation. qPCR analysis of Cxcl10 in (FIG. 8B) DNase I KO, (FIG. 8C) DNase II KO and (FIG. 8D) Trex1 KO macrophages at 6 hrs following engulfment of B16 cells containing STAVs. Error bars indicate s.d. *; p<0.05, Student's t-test.

FIG. 9A-9D. Anti-tumor activity of STAVs in B16 OVA melanomas. (FIG. 9A) Schematic representation of intratumoral injection of STAVs in B16 OVA melanoma. The mice were subcutaneously injected with B16-OVA cells on the flank. 10 ug of STAVs was injected intratumorally (i.t.) every three days. Tumor volumes from (FIG. 9B) WT (n=7/group) and (FIG. 9C) SKO mice (n=7/group) were measured on the indicated days. (FIG. 9D) Frequency of OVA specific CD8+ T cells in the spleen from WT (n=4/group) and SKO (n=4/group) mice injected with STAV or PBS as control. Error bars indicate s.d. *; p<0.05, Student's t-test.

FIG. 10A-10G. Protection of lung metastasis by B16 OVA requires STING. (FIG. 10A) Schematic representation of the dead cell immunization. B16 OVA cells were transfected by STAVs for 3 hours and irradiated by UV (120 mJ/cm). After 24 hours, WT, SKO, TLR9 KO, and cGAS KO mice were i.p. injected with the irradiated B16 cells with/without STAV, twice every week. (FIG. 10B) IFNγ measurement in splenocytes from WT, SKO, TLR9 KO, and cGAS KO mice at 7 days after the second immunization. (FIG. 10C) Schematic representation of post-vaccination for B16 OVA mediated lung metastasis. WT, TLR9KO, SKO, and cGAS KO mice were I.V. injected with B16 OVA cells. On day 1, 3, 7, and 14, the mice were IP injected by UV irradiated B16 OVA cells ($1 \times 10^5$ cells/mouse) with STAVs. Survival rates from (FIG. 10D) WT (p=0.0429, n=7/group), (FIG. 10E) SKO (p=0.2616, n=7/group), (FIG. 10F) cGAS KO (p=0.4075, n=7/group), and (FIG. 10G) TLR9K0 (p=0.0012 n=7/group) mice were monitored. P values are based on Logrank test, with P<0.05 considered statistically significant.

FIG. 11. Fold changes of gene array analysis in B16 cells transfected with STAVs. Gene expression fold changes of ILLUMINA array of B16 cells transfected with STAVs. Fold change analysis was performed between two groups and differentially expressed genes were selected based on threshold of Fold change ≥3 from a comparison between untransfected and STAVs transfected B16 cells.

FIG. 12. Fold changes of gene array analysis in B16 feeding macrophages. Gene expression fold changes of ILLUMINA array.

DETAILED DESCRIPTION

Figure 1I:
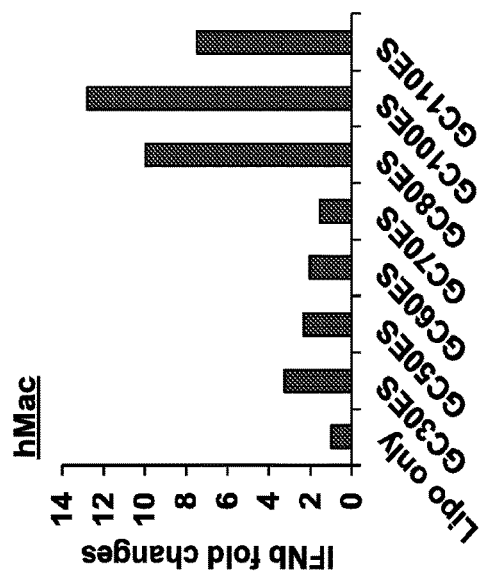
Figure 1H:
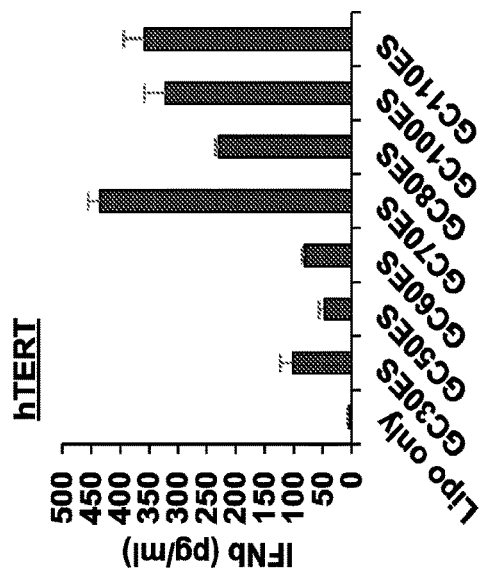
Figure 1G:
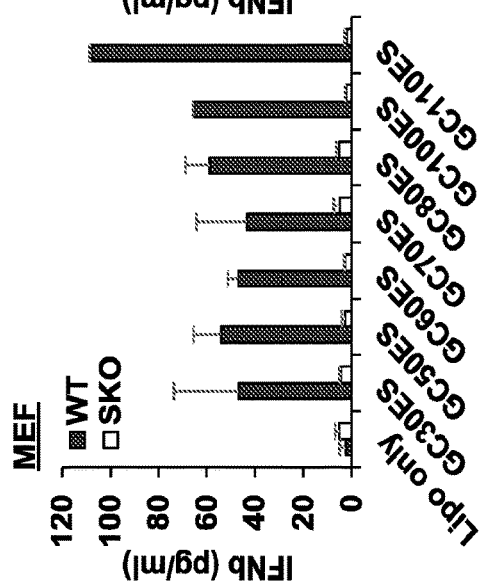

Unless otherwise defined, all technical and scientific terms used herein have the same meaning as commonly understood by one of ordinary skill in the art to which this invention belongs. The following references provide one of skill with a general definition of many of the terms used in this invention: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

Each publication, patent application, patent, and other reference cited herein is incorporated by reference in its entirety to the extent that it is not inconsistent with the present disclosure.

It is noted here that, as used in this specification and the appended claims, the singular forms "a," "an," and "the" include plural reference unless the context clearly dictates otherwise.

As used herein, the following terms have the meanings ascribed to them unless specified otherwise.

Definitions

The term "induces or enhances an immune response" as used herein refers to causing a statistically measurable induction or increase in an immune response over a control sample to which the peptide, polypeptide or protein has not been administered. Preferably the induction or enhancement of the immune response results in a prophylactic or therapeutic response in a subject. Examples of immune responses are increased production of type I IFN, increased resistance to viral and other types of infection by alternate pathogens. The enhancement of immune responses to tumors (anti-tumor responses), or the development of vaccines to prevent tumors or eliminate existing tumors.

The term "STING" as used herein includes, without limitation, nucleic acids, polynucleotides, oligonucleotides, sense and antisense polynucleotide strands, complementary sequences, peptides, polypeptides, proteins, homologous and/or orthologous STING molecules, isoforms, precursors, mutants, variants, derivatives, splice variants, alleles, different species, and active fragments thereof.

A "STING activator" or "STAV" as used herein refers to a nucleotide that when introduced into or produced by a cell can induce signaling through the STING protein. In nature, cyclic dinucleotides (CDN) are natural activators of STING, but are not often induced in tumor cells, or are used by tumor cells to evade tumor cell death. It is contemplated herein that the STAV is a double standard DNA molecule that when introduced into the cytosol of a cell activates STING signaling. The STAV dsDNA may have a modified 5' end and/or may have modified bases every 2, 3, 4 or 5 nucleotides throughout the nucleotide sequences. In various embodiments, the STAV is about 20 to 90, 25 to 90, or 30 to 70 nucleotides in length, or about 20, 25, 30, 35, 40, 45, 50, 55, 60, 65, 70, 75, 80, 85 or 90 nucleotides in length.

A "DNA Vaccine" or "DNA vector" as used herein refers to a synthetic DNA structure that can be transcribed in target cells and can comprise a linear nucleic acid such as a purified DNA, a DNA incorporated in a plasmid vector, or a DNA incorporated into any other vector suitable for introducing DNA into a host cell. In various embodiments, the DNA vaccine can be naked DNA. Provided herein is a naked DNA vaccine, a plasmid DNA vaccine or a viral vector vaccine. It is contemplated that the vaccine is a live viral vaccine, live attenuated viral vaccine, or inactivated or killed viral vaccine. In various embodiments, the vaccine may comprise virus-like particles (VLPs).

"Vesicular stomatitis virus" or "VSV" as used herein refers to any strain of VSV or mutant forms of VSV, such as those described in WO 01/19380 or US20140088177. A VSV construct herein may be in any of several forms, including, but not limited to, genomic RNA, mRNA, cDNA, part or all of the VSV RNA encapsulated in the nucleocapsid core, VSV complexed with compounds such as PEG and VSV conjugated to a nonviral protein. VSV vectors useful herein encompass replication-competent and replication-defective VSV vectors, such as, VSV vectors lacking G glycoprotein.

As used herein, the term "vector" refers to a polynucleotide construct designed for transduction/transfection of one or more cell types. VSV vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors", which comprise the attributes of more than one type of vector. The present invention encompasses viral vectors, such as vesicular stomatitis virus (VSV), a lentivirus, an acdenovirus, an adeno-associated virus, a vaccinia virus, or a modified vaccinia Ankara (MVA) virus vectors that comprise nucleic acid encoding Zika virus proteins, such as an Env protein. It is contemplated that the vectors can comprises a polynucleotide encoding a Zika protein as well as a polynucleotide encoding another protein that may improve efficacy of the vector, such as cytokines, including but not limited to those cytokines described herein; chemokines, such as for example, Mip; co-stimulatory proteins, such as for example, B7-1 and B7-2; angiostatin; endostatin; and heat shock proteins, such as for example gp96.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, genomic RNA, mRNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P—NH2) or a mixed phosphoramidate-phosphodiester oligomer. Peyrottes et al. (1996) Nucleic Acids Res. 24: 1841-8; Chaturvedi et al. (1996) Nucleic Acids Res. 24: 2318-23; Schultz et al. (1996) Nucleic Acids Res. 24: 2966-73. A phosphorothioate linkage can be used in place of a phosphodiester linkage. Braun et al. (1988) J. Immunol. 141: 2084-9; Latimer et al. (1995) Molec. Immunol. 32: 1057-1064. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. Reference to a polynucleotide sequence (such as referring to a SEQ ID NO) also includes the complement sequence.

The following are non-limiting examples of polynucleotides: a gene or gene fragment, exons, introns, genomic RNA, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Under transcriptional control" is a term well understood in the art and indicates that transcription of a polynucleotide sequence depends on its being operably (operatively) linked to an element which contributes to the initiation of, or promotes, transcription. "Operably linked" refers to a juxtaposition wherein the elements are in an arrangement allowing them to function.

As used herein, in the context of the viral vectors, a "heterologous polynucleotide" or "heterologous gene" or "transgene" is any polynucleotide or gene that is not present in wild-type viral vector.

As used herein, in the context of the vectors, a "heterologous" promoter is one which is not associated with or derived from the vector itself.

A "host cell" includes an individual cell or cell culture which can be or has been a recipient of a vector(s) described herein. Host cells include progeny of a single host cell, and the progeny may not necessarily be completely identical (in morphology or in total DNA complement) to the original parent cell due to natural, accidental, or deliberate mutation and/or change. A host cell includes cells transfected, transformed or infected in vivo or in vitro with a vector herein.

A "vector" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest in gene therapy. Vectors include, for example, viral vectors (such as adenoviruses ("Ad"), adeno-associated viruses (AAV), and vesicular stomatitis virus (VSV) and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Other vectors include those described by Chen et al; BioTechniques, 34: 167-171 (2003). A large variety of such vectors are known in the art and are generally available.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

As used herein, "vaccine" refers to a composition comprising a vector comprising a STING activator as described herein, which is useful in the treatment of cancer or other conditions in which enhanced immune response is indicated. It is contemplated that the vaccine comprises a pharmaceutically acceptable carrier and/or an adjuvant. It is contemplated that vaccines are prophylactic or therapeutic. A "prophylactic" treatment is a treatment administered to a subject who does not exhibit signs of a disease or exhibits only early signs for the purpose of decreasing the risk of developing pathology. The compounds of the invention may be given as a prophylactic treatment to reduce the likelihood of developing a pathology or to minimize the severity of the pathology, if developed. A "therapeutic" treatment is a treatment administered to a subject who exhibits signs or symptoms of pathology for the purpose of diminishing or eliminating those signs or symptoms. The signs or symptoms may be biochemical, cellular, histological, functional, subjective or objective.

"An antigen presenting cell" (APC) is a cell that is capable of activating T cells, and includes, but is not limited to, monocytes/macrophages, B cells and dendritic cells (DCs). The term "dendritic cell" or "DC" refers to any member of a diverse population of morphologically similar cell types found in lymphoid or non-lymphoid tissues. These cells are characterized by their distinctive morphology, high levels of surface MHC-class II expression. DCs can be isolated from a number of tissue sources. DCs have a high capacity for sensitizing MHC-restricted T cells and are very effective at presenting antigens to T cells in situ. The antigens may be self-antigens that are expressed during T cell development and tolerance, and foreign antigens that are present during normal immune processes.

The "treatment of cancer", refers to one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

As used herein, "isolated" refers to a polynucleotide, virus or antigenic composition that is removed from its native environment. Thus, an isolated biological material is free of some or all cellular components, i.e., components of the cells in which the native material occurs naturally (e.g., cytoplasmic or membrane component). In one aspect, a polynucleotide, virus or antigenic composition is deemed isolated if it is present in a cell extract or supernatant. In the case of nucleic acid molecules, an isolated nucleic acid includes a PCR product, an isolated mRNA, a cDNA, or a restriction fragment.

"Purified" as used herein refers to a virus or immunogenic composition that has been isolated under conditions that reduce or eliminate the presence of unrelated materials, i.e., contaminants, including endogenous materials from which the composition is obtained. By way of example, and without limitation, a purified virion is substantially free of host cell or culture components, including tissue culture or cell proteins and non-specific pathogens. In various embodiments, purified material substantially free of contaminants is at least 50% pure; at least 60%, at least 70%, at least 80%, at least 90%, at least 95%, at least 96%, at least 97%, at least 98% or even at least 99% pure. Purity can be evaluated by chromatography, gel electrophoresis, immunoassay, composition analysis, biological assay, and other methods known in the art.

As used herein, "pharmaceutical composition" refers to a composition suitable for administration to a subject animal, including humans and mammals. A pharmaceutical composition comprises a pharmacologically effective amount of a virus or antigenic composition of the invention and also comprises a pharmaceutically acceptable carrier. A pharmaceutical composition encompasses a composition comprising the active ingredient(s), and the inert ingredient(s) that make up the pharmaceutically acceptable carrier, as well as any product which results, directly or indirectly, from combination, complexation or aggregation of any two or more of the ingredients. Accordingly, the pharmaceutical compositions of the present invention encompass any composition made by admixing a compound or conjugate of the present invention and a pharmaceutically acceptable carrier.

As used herein, "pharmaceutically acceptable carrier" include any and all clinically useful solvents, dispersion media, coatings, antibacterial and antifungal agents, isotonic and absorption delaying agents, buffers, and excipients, such as a phosphate buffered saline solution, 5% aqueous solution of dextrose or mannitol, and emulsions, such as an oil/water or water/oil emulsion, and various types of wetting agents and/or adjuvants. Suitable pharmaceutical carriers and formulations are described in Remington's Pharmaceutical Sciences, 19th Ed. (Mack Publishing Co., Easton, 1995). Pharmaceutical carriers useful for the composition depend upon the intended mode of administration of the active agent. Typical modes of administration include, but are not limited to, enteral (e.g., oral) or parenteral (e.g., subcutaneous, intramuscular, intravenous or intraperitoneal injection; or topical, transdermal, or transmucosal administration). A "pharmaceutically acceptable salt" is a salt that can be formulated into a compound or conjugate for pharmaceutical use including, e.g., metal salts (sodium, potassium, magnesium, calcium, etc.) and salts of ammonia or organic amines.

As used herein, "pharmaceutically acceptable" or "pharmacologically acceptable" refers to a material which is not biologically or otherwise undesirable, i.e., the material may be administered to an individual without causing any undesirable biological effects or interacting in a deleterious manner with any of the components of the composition in which it is contained, or when administered using routes well-known in the art, as described below.

As used herein, a "condition" or "disorder" associated with a "target" in which modification of target activity described herein is beneficial and also includes other disorders in which high levels of target have been shown to be or are suspected of being either responsible for the pathophysiology of the disorder or a factor that contributes to a worsening of the disorder, as well as diseases and other disorders in which modulation of the target is associated with changes in clinical signs or symptoms. Such disorders may be evidenced, for example, by an increase in the levels of target secreted and/or on the cell surface and/or modified target signaling in the affected cells or tissues of a subject suffering from the disorder. Exemplary diseases, conditions or disorders that can be treated with a STING activator are described in more detail in the Detailed Description.

STING (Stimulator of Interferon Genes)

STING (Stimulator of Interferon Genes), a molecule that plays a key role in the innate immune response, includes 5 putative transmembrane (TM) regions, predominantly resides in the endoplasmic reticulum (ER), and is able to activate both NF-κB and IRF3 transcription pathways to induce type I IFN and to exert a potent anti-viral state following expression. Human STING is a 379 amino acid protein, having an amino acid sequence set out in Genbank Accession No. NP_938023 and nucleotide sequence set out in Genbank Accession No. NM_198282, though alternate protein isoforms may exist (Genbank Accession Nos. NP_001288667.1, XP_011535942.1, XP_011535941.1). See e.g., U.S. patent publication 20130039933 and PCT/US2009/052767, herein incorporated by reference in their entirety. The amino acid sequence of human STING (379 amino acids) is set out below (SEQ ID NO: 3): M P H S S L H P S I P C P R G H G A Q K A A L V L L S A C L V T L W G L G E P P E H T L R Y L V L H L A S L Q L G L L L N G V C S L A E E L R H I H S R Y R G S Y W R T V R A C L G C P L R R G A L L L L S I Y F Y Y S L P N A V G P P F T W M L A L L G L S Q A L N I L L G L K G L A P A E I S A V C E K G N F N V A H G L A W S Y Y I G Y L R L I L P E L Q A R I R T Y N Q H Y N N L L R G A V S Q R L Y I L L P L D C G V P D N L S M A D P N I R F L D K L P Q Q T G D H A G I K D R V Y S N S I Y E L L E N G Q R A G T C V L E Y A T P L Q T L F A M S Q Y S Q A G F S R E D R L E Q A K L F C R T L E D I L A D A P E S Q N N C R L I A Y Q E P A D D S S F S L S Q E V L R H L R Q E E K E E V T V G S L K T S A V P S T S T M S Q E P E L L I S G M E K P L P L R T D F S.

Loss of STING reduced the ability of polyI:C to activate type I IFN and rendered murine embryonic fibroblasts lacking STING ($^{-/-}$ MEFs) generated by targeted homologous recombination, susceptible to vesicular stomatitis virus (VSV) infection. In the absence of STING, DNA-mediated type I IFN responses were inhibited, indicating that STING may play an important role in recognizing DNA from viruses, bacteria, and other pathogens which can infect cells. Yeast-two hybrid and co-immunoprecipitation studies indicated that STING interacts with RIG-I and with Ssr2/TRAPβ, a member of the translocon-associated protein (TRAP) complex required for protein translocation across the ER membrane following translation. RNAi ablation of TRAPβ inhibited STING function and impeded the production of type I IFN in response to polyIC.

Further experiments showed that STING itself binds nucleic acids including single- and double-stranded DNA such as from pathogens and apoptotic DNA, and plays a central role in regulating proinflammatory gene expression in inflammatory conditions such as DNA-mediated arthritis and cancer. Certain inhibitors and activators of STING are discussed in International Patent Publication No. WO 2013/166000.

STING Activators

In nature, cyclic dinucleotides (CDN) are natural activators of STING, but are not often induced in tumor cells, or are used by tumor cells to evade tumor cell death. CDNs typically stay in the nucleus and are not leaked into the cytosol, which helps tumors evade immune cells. In order to use the advantages of STING in cancer, the inventors developed a nucleotide that could stay in the cytosol and induce STING activation in response to free dsDNA, similar to the situation in apoptosis of a cell.

It is contemplated herein that the STAV is a double stranded DNA molecule that when introduced into the cytosol of a cell activates STING signaling.

In various embodiments, the STAV is about 20 to 90, 25 to 90, or 30 to 70 nucleotides in length, or about 20, 25, 30, 35, 40, 45, 50, 55, 60, 65, 70, 75, 80, 85 or 90 nucleotides in length.

In various embodiments, the activator oligonucleotide herein is AT (adenine-thymine) rich or GC (guanine-cytosine) rich. For example, the activator sequence may consist of all A residues, all T residues, alternating A and T residues, or a mixture of A and T residues, e.g., wherein approximately 20, 30, 40, 50, 60, 70, 80 or 90% or more of the nucleotides are A residues or T residues, and the remaining residues are the complementary nucleotide. It is also contemplated that the activator sequence may consist of all G residues, all C residues, alternating G and C residues, or a mixture of G and C residues, e.g., wherein approximately 20, 30, 40, 50, 60, 70, 80 or 90% or more of the nucleotides are G residues or C residues, and the remaining residues are the complementary nucleotide. Further, the activator polynucleotide may be a mixture of A, T, G and C nucleotides. In various embodiments, the activator has a sequence as follows: Sense strand: AAAAAAAAAAAAAA-AAAAAAAAAAAAAAAAAAAAAAAAAAAAAAAA- AAAAAAA AAAAAAAAAAAAAAAAAAAAAAA- AAAAAAAAAAAA (SEQ ID NO: 1), optionally wherein the first three and last three nucleotides are modified by phosphorothioate linkage;

Anti-Sense strand: TTTTTTTTTTTTTTTTTTTTTT- TTTTTTTTTTTTTTTTTTTTTTTTTTTTTTTTTTT- TTT TTTTTTTTTTTTTTTTTTTTTTTTT (SEQ ID NO: 2), optionally wherein the first three and last three nucleotides are modified by phosphorothioate linkage.

The STAV dsDNA may have a modified 5' end and/or may have modified bases every 2, 3, 4 or 5 nucleotides throughout the nucleotide sequences. The 5' end and/or 3' end may be modified. In some embodiments, the 5' end is modified by phosphorothioate linkage. In some embodiments, the 3' end is modified by phosphorothioate linkage. In some embodiments, the first three nucleotides at the 5' end are modified by phosphorothioate linkage. In some embodiments, the last three nucleotides at the 3' end are modified by phosphorothioate linkage. In various embodiments, the activator nucleotide is modified every 2, 3, 4, or 5 nucleotides. In various embodiments, the activator nucleotide is modified at every third base.

In one embodiment, a STAV oligonucleotide may comprise combinations of phosphorothioate internucleotide linkages and at least one internucleotide linkage selected from the group consisting of: alkylphosphonate, phosphorodithioate, alkylphosphonothioate, phosphoramidate, carbamate, carbonate, phosphate triester, acetamidate, carboxymethyl ester, and/or combinations thereof.

In another embodiment, a STAV oligonucleotide optionally comprises at least one modified nucleobase comprising, peptide nucleic acids, locked nucleic acid (LNA) molecules, analogues, derivatives and/or combinations thereof.

Oligonucleotides may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N.sub.6 (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, may be included. 5-Me-C substitutions have been shown to increase nucleic acid duplex stability by 0.6-1.2.degree. C. (Sanghvi, Y. S., in Crooke, S. T. and Lebleu, B., eds., Antisense Research and Applications, CRC Press, Boca Raton, 1993, pp. 276-278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., Proc. Natl. Acad. Sci. USA 1989, 86, 6553), cholic acid (Manoharan et al. Bioorg. Med. Chem. Let. 1994, 4, 1053), a thioether, e.g., hexyl-5-tritylthiol (Manoharan et al. Ann. N.Y. Acad. Sci. 1992, 660, 306; Manoharan et al. Bioorg. Med. Chem. Let. 1993, 3, 2765), a thiocholesterol (Oberhauser et al., Nucl. Acids Res. 1992, 20, 533), an aliphatic chain, e.g., dodecandiol or undecyl residues (Saison-Behmoaras et al. EMBO J. 1991, 10, 111; Kabanov et al. FEBS Lett. 1990, 259, 327; Svinarchuk et al. Biochimie 1993, 75, 49), a phospholipid, e.g., di-hexadecyl-rac-glycerol or triethylammonium 1,2-di-O-hexadecyl-rac-glycero-3-H-phosphonate (Manoharan et al. Tetrahedron Lett. 1995, 36, 3651; Shea et al. Nucl. Acids Res. 1990, 18, 3777), a polyamine or a polyethylene glycol chain (Manoharan et al. Nucleosides & Nucleotides 1995, 14, 969), or adamantane acetic acid (Manoharan et al. Tetrahedron Lett. 1995, 36, 3651). Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

In another embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

In accordance with the disclosure, use of modifications such as the use of LNA monomers to enhance the potency, specificity and duration of action and broaden the routes of administration of oligonucleotides comprised of current chemistries such as MOE, ANA, FANA, PS etc. (ref: Recent advances in the medical chemistry of antisense oligonucleotide by Uhlman, Current Opinions in Drug Discovery & Development 2000 Vol 3 No 2). This can be achieved by substituting some of the monomers in the current oligonucleotides by LNA monomers. The LNA modified oligonucleotide may have a size similar to the parent compound or may be larger or preferably smaller. It is preferred that such LNA-modified oligonucleotides contain less than about 70%, more preferably less than about 60%, most preferably less than about 50% LNA monomers and that their sizes are between about 5 and 25 nucleotides, more preferably between about 12 and 20 nucleotides.

Preferred modified oligonucleotide backbones comprise, but not limited to, phosphorothioates, chiral phosphorothioates, phosphorodithioates, phosphotriesters, aminoalkylphosphotriesters, methyl and other alkyl phosphonates comprising 3' alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone.

In another preferred embodiment of the invention the oligonucleotides with phosphorothioate backbones and oligonucleosides with heteroatom backbones, and in particular-$CH_2$—NH—O—$CH_2$—, —$CH_2$—N($CH_3$)—O—$CH_2$- known as a methylene (methylimino) or MMI backbone, —$CH_2$—O—N($CH_3$)—$CH_2$—, —$CH_2$N($CH_3$)—N($CH_3$) $CH_2$-and-O—N($CH_3$)—$CH_2$—CH2— wherein the native phosphodiester backbone is represented as —O—P—O—$CH_2$— of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O alkyl-O-alkyl, wherein the alkyl, alkenyl and alkynyl may be substituted or unsubstituted C to C0 alkyl or $C_2$ to C0 alkenyl and alkynyl. Particularly preferred are O($CH_2$). On, $CH_3$, O($CH_2$), $OCH_3$, O($CH_2$)$_n$$NH_2$, O($CH_2$)$_n$$CH_3$, O($CH_2$)$_n$$ONH_2$, and O($CH_2$)$_n$ON($CH_2$)$_n$$CH_3$)$_2$ where n and m can be from 1 to about 10. Other preferred oligonucleotides comprise one of the following at the 2' position: C to CO, (lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification comprises 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further preferred modification comprises 2'-dimethylaminooxyethoxy, i.e., a O($CH_2$)$_2$ON($CH_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$.

Other preferred modifications comprise 2'-methoxy (2'-O $CH_3$), 2'-aminopropoxy (2'-O$CH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also comprise nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in 'The Concise Encyclopedia of Polymer Science And Engineering', pages 858-859, Kroschwitz, J. I., ed. John Wiley & Sons, 1990, those disclosed by Englisch et al., 'Angewandle Chemie, International Edition', 1991, 30, page 613, and those disclosed by Sanghvi, Y. S., Chapter 15, 'Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These comprise 5-substituted pyrimidines, 6-azapyrimidines and N-2, N-6 and 0-6 substituted purines, comprising 2-aminopropyladenine, 5-propynyluracil and 5-propynylcytosine.

5-methylcytosine substitutions have been shown to increase nucleic acid duplex stability by 0.6-1.2° C. (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications.

Methods of Use

In various embodiments, the disclosure provides a method of activating STING in a subject in need thereof comprising administering a composition comprising an activator of STING described herein, wherein the activator induces STING signaling.

Further contemplated is a method of stimulating an immune response in a subject in need thereof comprising administering a composition comprising an activator of STING described herein. In various embodiments, the immune response is an ongoing immune response in cancer, a microbial infection or an autoimmune disease. In various embodiments, the STING activator may be administered prophylactically in a disease or disorder in which an immune response is in a remission phase, e.g., in cancer or an autoimmune disease.

In one embodiment, the disclosure provides a method of decreasing the size of a tumor in a subject having a tumor or cancer comprising administering a composition comprising an activator of STING. Also provided is a method for treating cancer or preventing the recurrence of cancer comprising administering to a subject in need thereof a therapeutically effective amount of a STAV or a pharmaceutical composition comprising a STAV or vector or vaccine comprising a STAV as described herein.

Exemplary conditions or disorders that can be treated with STAVs include cancers, such as esophageal cancer, pancreatic cancer, metastatic pancreatic cancer, metastatic adenocarcinoma of the pancreas, bladder cancer, stomach cancer, fibrotic cancer, glioma, malignant glioma, diffuse intrinsic pontine glioma, recurrent childhood brain neoplasm renal cell carcinoma, clear-cell metastatic renal cell carcinoma, kidney cancer, prostate cancer, metastatic castration resistant prostate cancer, stage IV prostate cancer, metastatic melanoma, melanoma, malignant melanoma, recurrent melanoma of the skin, melanoma brain metastases, stage IIIA skin melanoma; stage IIIB skin melanoma, stage IIIC skin melanoma; stage IV skin melanoma, malignant melanoma of head and neck, lung cancer, non-small cell lung cancer (NSCLC), squamous cell non-small cell lung cancer, breast cancer, recurrent metastatic breast cancer, hepatocellular carcinoma, hodgkin's lymphoma, follicular lymphoma, non-hodgkin's lymphoma, advanced B-cell NHL, HL including diffuse large B-cell lymphoma (DLBCL), multiple myeloma, chronic myeloid leukemia, adult acute myeloid leukemia in remission; adult acute myeloid leukemia with Inv(16)(p13.1q22); CBFB-MYH11; adult acute myeloid leukemia with t(16;16)(p13.1;q22); CBFB-MYH11; adult acute myeloid leukemia with t(8;21)(q22;q22); RUNX1-RUNX1T1; adult acute myeloid leukemia with t(9;11)(p22;q23); MLLT3-MLL; adult acute promyelocytic leukemia with t(15;17)(q22;q12); PML-RARA; alkylating agent-related acute myeloid leukemia, chronic lymphocytic leukemia, richter's syndrome; waldenstrom macroglobulinemia, adult glioblastoma; adult gliosarcoma, recurrent glioblastoma, recurrent childhood rhabdomyosarcoma, recurrent Ewing sarcoma/peripheral primitive neuroectodermal tumor, recurrent neuroblastoma; recurrent osteosarcoma, colorectal cancer, MSI positive colorectal cancer; MSI negative colorectal cancer, nasopharyngeal nonkeratinizing carcinoma; recurrent nasopharyngeal undifferentiated carcinoma, cervical adenocarcinoma; cervical adenosquamous carcinoma; cervical squamous cell carcinoma; recurrent cervical carcinoma; stage IVA cervical cancer; stage IVB cervical cancer, anal canal squamous cell carcinoma; metastatic anal canal carcinoma; recurrent anal canal carcinoma, recurrent head and neck cancer; carcinoma, squamous cell of head and neck, head and neck squamous cell carcinoma (HNSCC), ovarian carcinoma, colon cancer, gastric cancer, advanced GI cancer, gastric adenocarcinoma; gastroesophageal junction adenocarcinoma, bone neoplasms, soft tissue sarcoma; bone sarcoma, thymic carcinoma, urothelial carcinoma, recurrent merkel cell carcinoma; stage III merkel cell carcinoma; stage IV merkel cell carcinoma, myelodysplastic syndrome and recurrent mycosis fungoides and Sezary syndrome.

In some embodiments, cancers that can be treated with the present invention include ovarian cancer, colon cancer, melanoma, breast cancer or lung cancer.

It is contemplated that the methods herein reduce tumor size or tumor burden in the subject, and/or reduce metastasis in the subject. In various embodiments, the methods reduce the tumor size by 10%, 20%, 30% or more. In various embodiments, the methods reduce tumor size by 10%, 15%, 20%, 25%, 30%, 35%, 40%, 45%, 50%, 55%, 60%, 65%, 70%, 75%, 80%, 85%, 90%, 95% or 100%.

It is contemplated that the methods herein reduce tumor burden, and also reduce or prevent the recurrence of tumors once the cancer has gone into remission.

In various embodiments, the STAV or STAV compositions described herein modulates immune cells in a tumor. In some embodiments, the STAV or STAV compositions increases the number of macrophages or other phagocytes or antigen presenting cells in a tumor and/or increases phagocytic activity of cells in the area of the tumor.

Other conditions or disorders contemplated for treatment with a STAV as described herein include infectious diseases or autoimmune disease in which an increase in immune response may be desired. Exemplary conditions include, but are not limited to, an inflammatory bowel disease (e.g., ulcerative colitis or Crohn's disease), a peripheral vascular disease, a cerebral vascular accident (stroke), a disorder characterized by lesions having inflammatory cell infiltration, a disorder where amyloid plaques are present in the brain (e.g., Alzheimer's disease), Aicardi-Goutieres syndrome, juvenile arthritis, osteoporosis, amyotrophic lateral sclerosis, or multiple sclerosis.

Exemplary microbial infections contemplated include viral, bacterial or fungal infection.

Methods of Administration

Many methods may be used to administer or introduce the dsDNA STAVs or vectors, vaccines or viral particles comprising the dsDNA into individuals (i.e., including subjects or patients), including but not limited to, intratumorally, intravenously, intra-arterially, intraperitoneally, intranasally, intramuscularly, intradermally, subcutaneously, orally or by continuous infusion. The individual to which a vector or viral particle is administered is a primate, or in other examples, a mammal, or in other examples, a human, but can also be a non-human mammal including but not limited to cows, horses, sheep, pigs, fowl, cats, dogs, hamsters, mice and rats. In the use of a vector, vaccines or viral particles, the individual can be any animal in which a vector or virus is capable introducing the dsDNA and results in activation of STING.

The present invention encompasses compositions comprising dsDNA, vectors, vaccines or viral particles wherein said compositions can further comprise a pharmaceutically acceptable carrier. The amount of vector(s) to be administered will depend on several factors, such as route of administration, the condition of the individual, the degree of aggressiveness of the malignancy, and the particular vector employed. Also, the vector may be used in conjunction with other treatment modalities.

If administered as a viral vector(s), vaccines or viral particles from about $10^2$ up to about $10^7$ p.f.u., in other examples, from about $10^3$ up to about $10^6$ p.f.u., and in other examples, from about $10^4$ up to about $10^5$ p.f.u. is administered. If administered as a polynucleotide construct (i.e., not packaged as a virus), about 0.01 µg to about 100 µg of a viral construct of the present invention can be administered, in other examples, 0.1 µg to about 500 µg, and in other examples, about 0.5 µg to about 200 µg can be administered. More than one vector can be administered, either simultaneously or sequentially. Administrations are typically given periodically, while monitoring any response. Administration can be given, for example, intramuscularly, intravenously, intratumorally or intraperitoneally.

It is contemplated that an effective amount of the dsDNA, vector(s), vaccines or viral particles is administered. An "effective amount" is an amount sufficient to achieve a desired biological effect such as to induce enough humoral or cellular immunity. This may be dependent upon the type of vaccine, the age, sex, health, and weight of the recipient. Examples of desired biological effects include, but are not limited to, increase in immune response, increase in STING stimulation, decrease in tumor size or tumor burden, production of no symptoms or reduction in symptoms related to disease or condition being treated.

A vaccine or composition of the present invention is physiologically significant if its presence results in a detectable change in the physiology of a recipient patient that enhances at least one primary or secondary humoral or cellular immune response against a tumor or other targeted cell or microbe. For example, in certain embodiments, the STING activator increases infiltration of immune cells into the tumor or site of infection. In certain embodiments, the immune cells are macrophages, dendritic cells or other phaogcytes.

The composition, if desired, can also contain minor amounts of wetting or emulsifying agents or pH buffering agents. The composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Generally, the ingredients are supplied either separately or mixed together in unit dosage form, for example, as a dry lyophilized powder or water free concentrate in a hermetically sealed container such as an ampoule or sachet indicating the quantity of active agent. Where the composition is administered by injection, an ampoule of sterile diluent can be provided so that the ingredients may be mixed prior to administration.

Pharmaceutical compositions of the present disclosure containing the inhibitors described herein as an active ingredient may contain pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the present disclosure.

Formulation of the pharmaceutical composition will vary according to the route of administration selected (e.g., solution, emulsion). An appropriate composition comprising the inhibitor, e.g., an antibody, to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers.

A variety of aqueous carriers, e.g., sterile phosphate buffered saline solutions, bacteriostatic water, water, buffered water, 0.4% saline, 0.3% glycine, and the like, and may include other proteins for enhanced stability, such as albumin, lipoprotein, globulin, etc., subjected to mild chemical modifications or the like.

Therapeutic formulations of the inhibitors are prepared for storage by mixing the inhibitor having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules)

or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

The dose of vector, vaccine or viral particle to be employed in the formulation will also depend on the route of administration, and the nature of the patient, and should be decided according to the judgment of the practitioner and each patient's circumstances according to standard clinical techniques. The exact amount of vector or virus utilized in a given preparation is not critical provided that the minimum amount of virus necessary to produce immunologic activity is given. A dosage range of as little as about 10 mg, up to amount a milligram or more, is contemplated.

Effective doses of the vector or viral particle of the invention may also be extrapolated from dose-response curves derived from animal model test systems.

In one embodiment, administration is performed at the site of a cancer or affected tissue needing treatment by direct injection into the site or via a sustained delivery or sustained release mechanism, which can deliver the formulation internally. For example, biodegradable microspheres or capsules or other biodegradable polymer configurations capable of sustained delivery of a composition (e.g., a soluble polypeptide, antibody, or small molecule) can be included in the formulations of the disclosure implanted near or at site of the cancer.

Therapeutic compositions may also be delivered to the patient at multiple sites. The multiple administrations may be rendered simultaneously or may be administered over a period of time. In certain cases it is beneficial to provide a continuous flow of the therapeutic composition. Additional therapy may be administered on a period basis, for example, hourly, daily, every other day, twice weekly, three times weekly, weekly, every 2 weeks, every 3 weeks, monthly, or at a longer interval.

Combination Therapy

It is contemplated that a STAV of the present disclosure or composition thereof is administered with a second agent useful for treating a condition or disorder for which STAV therapy is used, e.g., cancer, infection or autoimmune disease.

Concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

The second agent may be other therapeutic agents, such as cytokines, growth factors, other inhibitors and antibodies to target antigens useful for treating cancer or immunological disorders, for example ipilimumab (YERVOY®, Bristol-Myers Squibb Company), an antibody to CTLA-4; bevacizumab (AVASTIN®, Genentech), an antibody to VEGF-A; erlotinib (TARCEVA®, Genentech and OSI Pharmaceuticals), a tyrosine kinase inhibitor which acts on EGFR, dasatinib (SPRYCEL®, Bristol-Myers Squibb Company), an oral Bcr-Abl tyrosone kinase inhibitor; IL-21; pegylated IFN-α2b; axitinib (INLYTA®, Pfizer, Inc.), a tyrosine kinase inhibitor; and trametinib (MEKINIST®, GlaxoSmithKline), a MEK inhibitor (Philips and Atkins, Int Immunol., 27(1):39-46 (2015) which is incorporated herein by reference).

It is contemplated the STAVs of the present disclosure and second agent may be given simultaneously, in the same formulation. It is further contemplated that the STAV and second agent are administered in a separate formulation and administered concurrently, with concurrently referring to agents given within 30 minutes of each other. It is further contemplated that the third agent may be given simultaneously with the inhibitors.

In another aspect, a STAV is administered prior to administration of the second agent. Prior administration refers to administration of a STAV within the range of one week prior to treatment with the second agent, up to 30 minutes before administration of the second agent. It is further contemplated that a STAV is administered subsequent to administration a second agent. Subsequent administration is meant to describe administration from 30 minutes after STAV treatment up to one week after STAV administration.

It is further contemplated that other adjunct therapies may be administered, where appropriate. For example, the patient may also be administered surgical therapy, chemotherapy, a cytotoxic agent, photodynamic therapy or radiation therapy where appropriate.

It is further contemplated that when the STAVs herein are administered in combination with a second agent, such as for example, wherein the second agent is a cytokine or growth factor, or a chemotherapeutic agent, the administration also includes use of a radiotherapeutic agent or radiation therapy. The radiation therapy administered in combination with an antibody composition is administered as determined by the treating physician, and at doses typically given to patients being treated for cancer.

A cytotoxic agent refers to a substance that inhibits or prevents the function of cells and/or causes destruction of cells. The term is intended to include radioactive isotopes (e.g., I131, I125, Y90 and Re186), chemotherapeutic agents, and toxins such as enzymatically active toxins of bacterial, fungal, plant or animal origin or synthetic toxins, or fragments thereof. A non-cytotoxic agent refers to a substance that does not inhibit or prevent the function of cells and/or does not cause destruction of cells. A non-cytotoxic agent may include an agent that can be activated to be cytotoxic. A non-cytotoxic agent may include a bead, liposome, matrix or particle (see, e.g., U.S. Patent Publications 2003/0028071 and 2003/0032995 which are incorporated by reference herein). Such agents may be conjugated, coupled, linked or associated with an antibody according to the disclosure.

Chemotherapeutic agents contemplated for use with the antibodies of the present disclosure include, but are not limited to those listed in Table I:

TABLE I

| Alkylating agents |
| --- |
| Nitrogen mustards |
| mechlorethamine |
| cyclophosphamide |
| ifosfamide |
| melphalan |
| chlorambucil |
| Nitrosoureas |
| carmustine (BCNU) |
| lomustine (CCNU) |
| semustine (methyl-CCNU) |
| Ethylenimine/Methyl-melamine |
| thriethylenemelamine (TEM) |
| triethylene thiophosphoramide |

TABLE I-continued (thiotepa)
hexamethylmelamine
(HMM, altretamine)
Alkyl sulfonates busulfan
Triazines dacarbazine (DTIC)
Antimetabolites
Folic Acid analogs methotrexate
Trimetrexate
Pemetrexed
(Multi-targeted antifolate)
Pyrimidine analogs 5-fluorouracil
fluorodeoxyuridine
gemcitabine
cytosine arabinoside
(AraC, cytarabine)
5-azacytidine
2,2'-difluorodeoxycytidine
Purine analogs 6-mercaptopurine
6-thioguanine
azathioprine
2'-deoxycoformycin
(pentostatin)
erythrohydroxynonyl-adenine (EHNA)
fludarabine phosphate
2-chlorodeoxyadenosine
(cladribine, 2-CdA)
Type I Topoisomerase Inhibitors camptothecin
topotecan
irinotecan
Biological response modifiers G-CSF
GM-CSF
Differentiation Agents retinoic acid derivatives
Hormones and antagonists
Adrenocorticosteroids/antagonists prednisone and equivalents
dexamethasone
ainoglutethimide
Progestins hydroxyprogesterone caproate
medroxyprogesterone acetate
megestrol acetate
Estrogens diethylstilbestrol
ethynyl estradiol/equivalents
Antiestrogen tamoxifen
Androgens testosterone propionate
fluoxymesterone/equivalents
Antiandrogens flutamide
gonadotropin-releasing
hormone analogs
leuprolide
Nonsteroidal antiandrogens flutamide
Natural products TABLE I-continued Antimitotic drugs
Taxanes paclitaxel
Vinca alkaloids
vinblastine (VLB)
vincristine
vinorelbine
Taxotere ® (docetaxel)
estramustine
estramustine phosphate
Epipodophylotoxins etoposide
teniposide
Antibiotics actimomycin D
daunomycin (rubidomycin)
doxorubicin (adriamycin)
mitoxantroneidarubicin
bleomycin
splicamycin (mithramycin)
mitomycinC
dactinomycin
aphidicolin
Enzymes L-asparaginase
L-arginase
Radiosensitizers metronidazole
misonidazole
desmethylmisonidazole
pimonidazole
etanidazole
nimorazole
RSU 1069
EO9
RB 6145
SR4233
nicotinamide
5-bromodeozyuridine
5-iododeoxyuridine
bromodeoxycytidine
Miscellaneous agents
Platinum coordination complexes cisplatin
Carboplatin
oxaliplatin
Anthracenedione
mitoxantrone
Substituted urea hydroxyurea
Methylhydrazine derivatives N-methylhydrazine (MIH)
procarbazine
Adrenocortical suppressant mitotane (o,p'- DDD)
ainoglutethimide
Cytokines interferon (α, β, γ)
interleukin-2
Photosensitizers hematoporphyrin derivatives
Photofrin ®
benzoporphyrin derivatives
Npe6
tin etioporphyrin (SnET2)
pheoboride-a
bacteriochlorophyll-a
naphthalocyanines
phthalocyanines TABLE I-continued zinc phthalocyanines
Radiation X-ray
ultraviolet light
gamma radiation
visible light
infrared radiation
microwave radiation Kits As an additional aspect, the disclosure includes kits which comprise one or more compounds or compositions packaged in a manner which facilitates their use to practice methods of the disclosure. In one embodiment, such a kit includes a compound or composition described herein (e.g., a composition comprising a target-specific antibody alone or in combination with another antibody or a third agent), packaged in a container such as a sealed bottle or vessel, with a label affixed to the container or included in the package that describes use of the compound or composition in practicing the method. Preferably, the compound or composition is packaged in a unit dosage form. The kit may further include a device suitable for administering the composition according to a specific route of administration or for practicing a screening assay. Preferably, the kit contains a label that describes use of the inhibitor compositions.

Additional aspects and details of the disclosure will be apparent from the following examples, which are intended to be illustrative rather than limiting.

Example 1

To further investigate the importance of STING in facilitating adaptive immune responses a variety of DNA-dependent nucleic acids were generated and their ability to activate STING signaling was examined.

Methods

Mice. STING knockout mice (SKO) were generated as described previously (Ishikawa and Barber, Nature 455:674-8, 2008) and have been backcrossed with C57BL/6J. Wild type C57BL/6J mice (WT) were provided from Jackson Laboratory. cGAS Knockout mice (cGAS KO) were kindly provided by Dr. Herbert W. Virgin I V (Washington University School of Medicine). TLR9 Knockout mice (TLR9KO) were purchased from Jackson Laboratory. Mice care and study were conducted under approval from the Institutional Animal Care and Use Committee of the University of Miami. Mouse genotypes from tail biopsies were determined by using real-time PCR with specific probes designed for each gene by commercial vendor (Transnetyx).

Cells. B16-OVA cells (B16) were kindly provided by Dr. Eli Gilboa (University of Miami) and cultured in complete Dulbecco's Modified Eagle Medium (DMEM, Invitrogen) including 10% heat-inactivated fetal calf serum (FCS, Invitrogen). 293, 293T cells and hTERT cells were purchased from ATCC. Mouse embryonic fibroblasts (MEFs) were obtained from e13.5 embryos by a standard procedure. Bone marrow derived macrophages (BMDM; MΦ) were isolated from hind-limb femurs of 8-10 weeks old WT, SKO, cGASKO, TLR9KO, DNase IKO, DNase II KO, or DNase III (Trex1) KO mice. Briefly, the marrow cells were flushed from the bones with complete DMEM with a 26 gauge needle. The cells were cultured in complete DMEM (Invitrogen) including 10 ng/ml of Mouse Recombinant Colony-Stimulating Factor (M-CSF, R&D Systems,) for 10 to 14 days.

STING-dependent, TLR9-independent adjuvants (STAVs). A ssDNA sense strand modified with Phosphorothioates (S-oligos) at the end (polyA90mer) was annealed to ssDNA antisense strand with same modification as antisense strand (polyT90mer); STAVs. Each oligos were synthesized and modified from TriLink Biotechnologies.

In vitro phagocytosis. MΦ was cultured as described above and seeded on 12 well plates ($2 \times 10^5$ cells/well). B16-OVA cells were transfected with STAVs at 3 ug/ml for 3 hours and irradiated by a UVC500 UV crosslinker at 120 mJ/cm$^2$ followed by 24 hour incubation. The treated B16-OVA cells were added to macrophages for 6 hours. Following vigorous washing to remove unengulfed B16-OVA cells, the macrophages were harvested for RNA extraction for qPCR and Gene array analysis. To check phagocytosis efficiency, macrophages were collected at 4 hours after phagocytosis and stained using APC-anti-mouse CD11b antibody (eBiosciences). Percentage of phagocytosed cells was assessed by flow cytometry using a LSRII instrument (Becton Dickinson, USA).

Gene Array Analysis. Total RNA was isolated from cells or tissues with RNeasy Mini kit (Qiagen). RNA quality was analyzed by Bionalyzer RNA 6000 Nano (Agilent Technologies). Gene array analysis was examined by Affymetrix Mouse Gene array (2.0 ST Array) at Hussman Institute for Human Genomics University of Miami. Gene expression profiles were processed and statistical analysis was performed at Public health science, University of Miami.

Quantitative Real-Time PCR (qPCR). Total RNA was extracted from cells using Trizol method and reverse transcribed by M-MLV reverse transcriptase (Promega). Real-time PCR was performed with the TaqMan gene Expression Assay (Ifn-β: Mm010439546, Cxcl10: Mm00445235; Applied Biosystems).

Cell death induction and analysis. B16-OVA cells were transfected with 3 µg/mL STAVs for 3 hours and then were treated by UV light (120 mJ/cm$^2$). After 24 hours at 37° C., 5% CO$_2$, cells were collected and fed to bone marrow-derived macrophages for 6 hours. B16-OVA cells viability was assessed by flow cytometric analysis with a FACSCantoII (Becton Dickinson, USA) after staining with 1 µg/mL propidium iodide (eBiosciences) and APC-labeled annexin V (eBiosciences).

Transfection efficiency. STAVs transfection efficiency into B16-OVA or 293T cells was evaluated by flow cytometry analysis. The cells were transfected with 3 µg/mL of FAM-labeled STAVs. After 24 hours, cells were collected and analyzed by flow cytometry using a LSRII instrument (Becton Dickinson, USA).

Antigen presentation assay. Bone marrow-derived macrophages were transfected with 3 µg/mL of STAVs for 24 hours and then pulsed with or without SIINFEKL (3 µM). After 2 hours, cells were stained with APC-labeled anti-H-2Kb-SIINFEKL (clone 25-D1.16) (Biolegend) and FITC-labeled anti-mouse CD11b (eBiosciences). Presentation of SIINFEKL on H-2Kb was evaluated by flow cytometry using a LSRII instrument (Becton Dickinson, USA).

Immunofluorescence staining. Cells were fixed with 4% paraformaldehyde in DMEM for 15 min at 37° C. and were permeabilized with 0.2% Triton X-100. Fixed and permeabilized cells were blocked with 10% BSA in PBS, incubated with primary antibodies in 2% BSA in PBS and then incubated with fluorophore-conjugated secondary antibodies (with Dapi counterstaining). After staining, cells were mounted in anti-fade mounting solution (Invitrogen) and examined under Leica SP5 spectral confocal inverted microscope.

Mass spectrometry analysis. The cells were transfected with 3 µg/mL of STAVs for 3 hrs or 1 µg/mL of pCMV or pcGAS plasmids for 24 hours. Following appropriate treatment, $1\times10^7$ cells were pelleted and snap-frozen in liquid nitrogen and stored at $-80°$ C. before further processing. To extract cGAMP, frozen cells were thawed on ice and lysed in cold 80% (vol/vol) methanol with 2% (vol/vol) acetic acid (HAc). Cyclic-di-GMP was supplemented as internal standard. Cell lysates were cleared by centrifugation at 4° C., 10,000×g for 10 min. Pellets were further extracted in 20% (vol/vol) methanol with 2% HAc twice and all extracts were pooled. cGAMP was then enriched by solid-phase extraction (SPE) using HyperSep Aminopropyl SPE Columns (Thermo Scientific) as previously described in Gao et al, 2015. Briefly, columns were activated by 100% methanol and washed twice with 2% HAc; after drawing through the extracts, columns were washed twice with 2% HAc and once with 80% methanol, and finally eluted with 2% (vol/vol) ammonium hydroxide in 80% methanol. The eluents were spin-vacuumed to dryness, reconstituted in liquid chromatography (LC)/MS-grade water and stored at $-20°$ C. before subject to LC/MS analysis. Chromatography was performed using a Thermo Scientific Surveyor MS Pump Plus pump and Micro AS autosampler. The separation was isocratic on a Water's XBridge Amide column (3.5 um, 2.1×100 mm) at 200 ul/min using 18:82 water:acetonitrile 6.3 mM ammonium hydroxide and 6.3 mM ammonium bicarbonate. The samples were introduced into a Thermo Scientific LTQ-FT, a hybrid mass spectrometer consisting of a linear ion trap and a Fourier transform ion cyclotron resonance mass spectrometer. The standard electrospray source was used operated in negative ion mode. cGAMP was quantitated using the m/z 522 product ion from the collision-induced dissociation of the deprotonated parent ion at m/z 673. An external calibration curve derived from eight standards [you can elaborate on the standards preparation if you wish] was used in the quantitation and acquired before and after the samples were analyzed. The c-di-GMP component was quantitated from the m/z 344 product ion originating from the deprotonated m/z 689 parent.

In vivo models. For anti-tumor effects, mice were subcutaneously injected with $5\times10^5$ cells of B16-OVA on the right flank. One week later, when tumors were 50 $mm^3$ in volume, 10 µg of STAVs was injected intratumorally (i.t.) every three days 3 times. The tumor volume was measured using calipers and calculated with the formula V=(length×$width^2$)/2. For post-vaccination in tumor bearing mice, mice were intravenously (i.v.) injected with B16 OVA cells ($1\times10^5$ cells/mouse). At 1, 3, 7, and 14 days, mice were injected intraperitoneally (i.p.) with UV irradiated B16 OVA cells ($1\times10^6$ cells/mouse). Survival rates were monitored for 110 days. B16-OVA cells were transfected with STAV at 3 µg/ml for 3 hours and irradiated by a UVC500 UV crosslinker at 120 $mJ/cm^2$ followed by 24 hours incubation.

OVA specific CD8+ T cell analysis and IFN γELISA. $1-2\times10^6$ splenocytes were stained with H-2Kb/SIINFEKL Pro5® Pentamer (ProImmune, UK) for 10 minutes at 22° C. Cells were then washed twice and incubated with FITC-labeled anti-mouse CD8 (eBiosciences) and PECy5-labeled anti-mouse CD19 (ProImmune, UK) antibodies for 20 minutes on ice, shielded from light. Following two further washes, cells were resuspended in fixative and analyzed by flow cytometry using a LSRII instrument (Becton Dickinson, USA). For IFNβ ELISA, $1\times10^6$ splenocytes were plated and stimulated with SIINFEKEL peptide (10 µg/ml). At 2 days after stimulation, the supernatant was harvested and IFNβ production was estimated by BD mouse IFNβ kit.

Statistical Analysis. All statistical analysis was performed by Student's t test. The data were considered to be significantly different when P<0.05.

Results

Figure 1J:
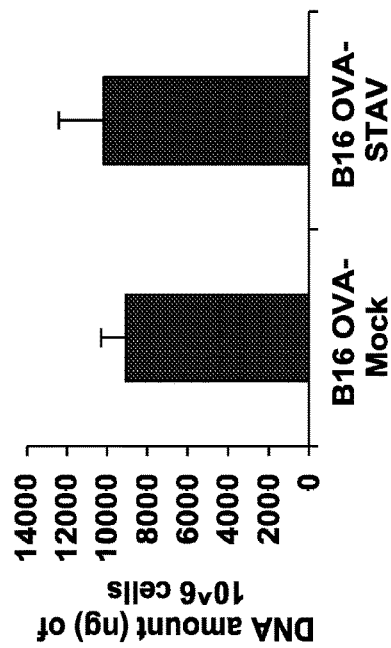
Figure 2A:
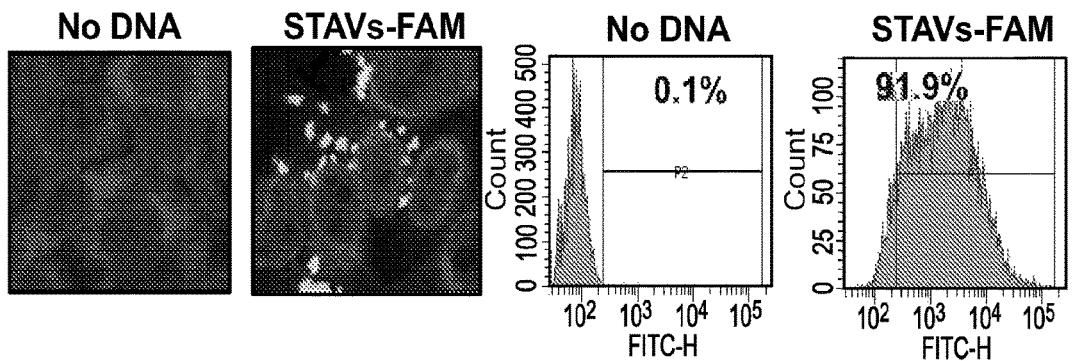
FIG. 2A-2L. Activation of macrophages by exogenous cytosolic DNA (STAVs) in engulfed apoptotic cells.
Figure 2B:
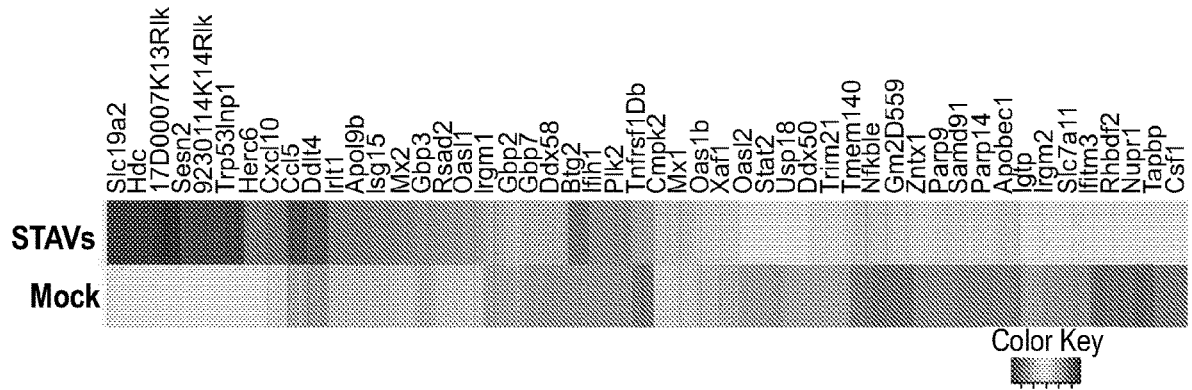
Figures 2C, 2D, 2E:
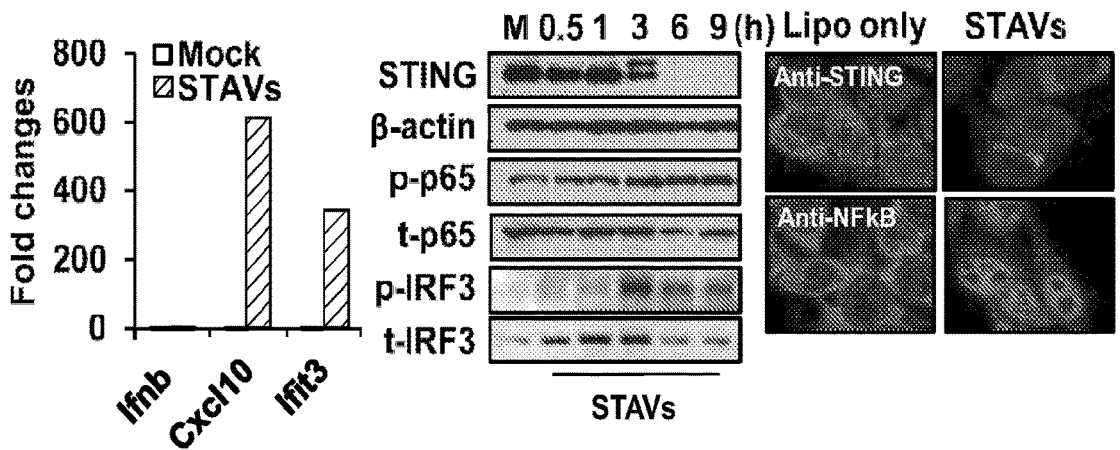
Figure 2F:
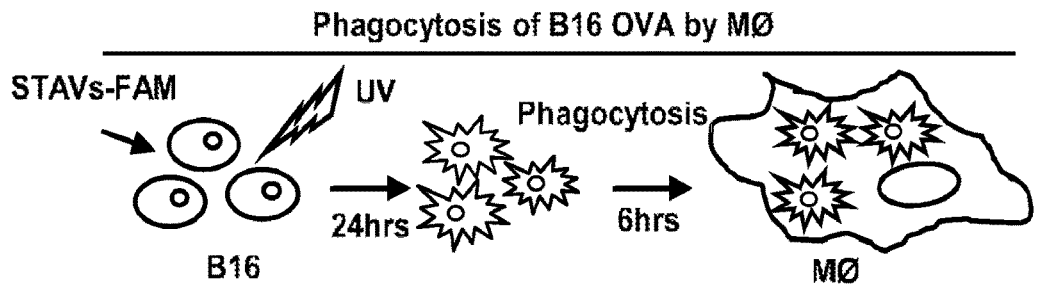
Figure 2G:
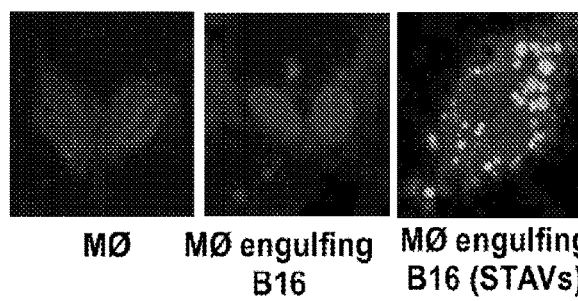
Figure 2H:
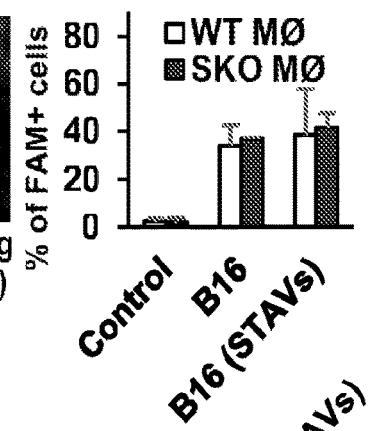
Figure 2I:
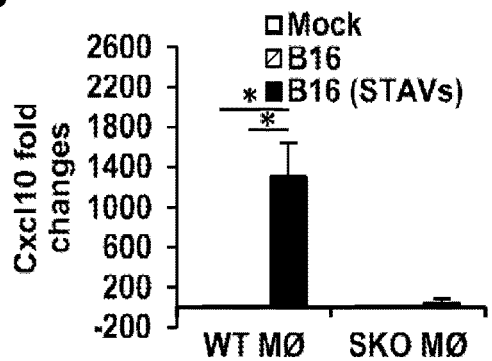
Figure 2J:
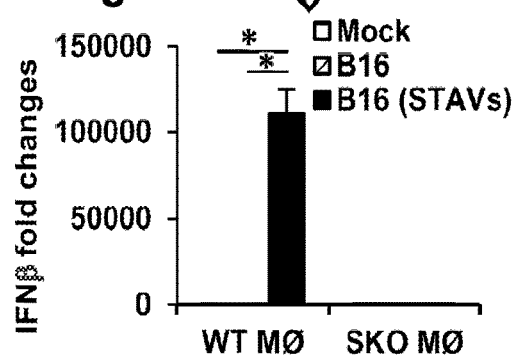
Figure 2K:
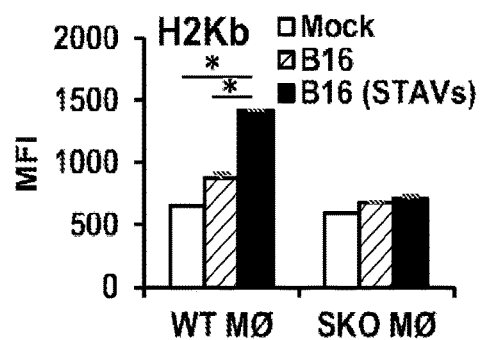
Figure 2L:
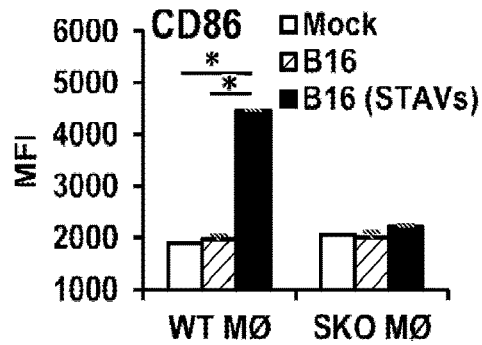

To further investigate the importance of STING in facilitating adaptive immune responses a variety of DNA-dependent nucleic acids were generated and examined for their ability to activate STING signaling. It was noted that transfected cytosolic dsDNA's, modified on the 5'end to help prevent exonuclease degradation, greater than approximately 30 bp in murine cells (MEFs; murine embryonic fibroblasts) or 70 bp in human cells (hTERT and primary human macrophages) were required for the efficient activation of STING (FIG. 1A-I). The effects, following transfection appeared to be largely independent of sequence specificity and both AT or GC rich structures were readily able to trigger STING activity. As a result of these endeavors, an AT rich STING activating dsDNA ligand of 90 bp with modified 5'-ends (referred to as STAV) was used for further study. Following the transfection of a variety of cells including murine B16 cells, it was observed that the majority of the STAVs remained in the cytosol of the cell in as yet undefined cellular compartments (FIG. 2A). Quantitation studies indicated that the cytosolic STAVs constituted approximately 1% of the total cellular DNA content as determined by quantitation analysis (FIG. 1J).

Figure 3A:
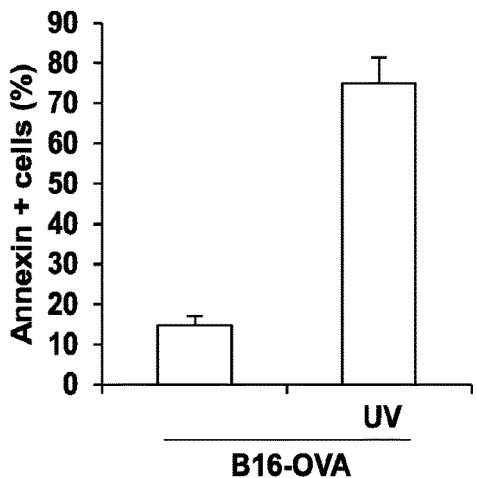
FIG. 3A-3D. B16 OVA cells to feed to macrophages. B16 OVA cells were transfected with 3 ug/ml of ISD-FITC for 24 hours and 48 hours.
Figure 3B:
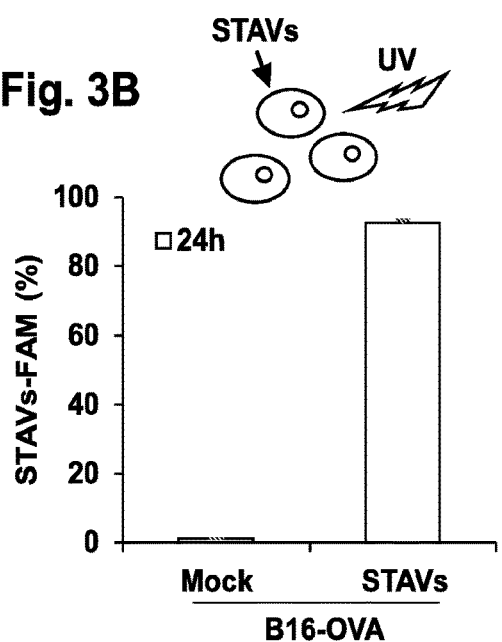
Figure 3C:
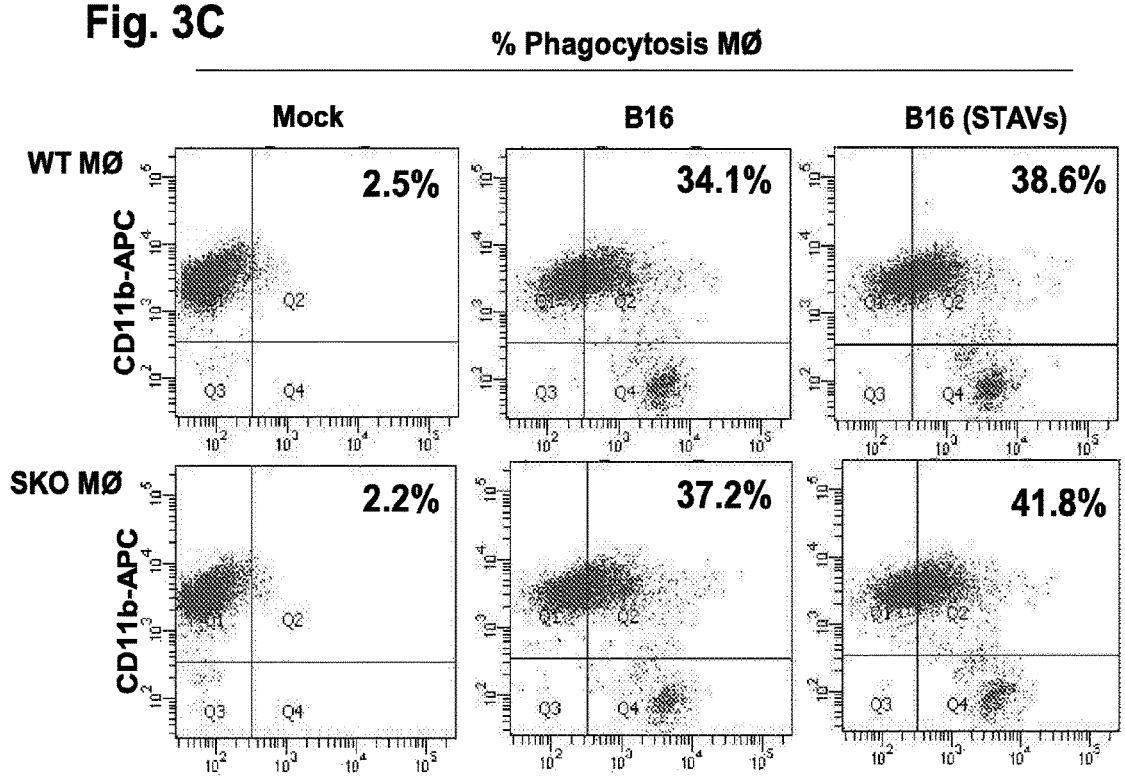
Figure 3D:
Figure 4A:
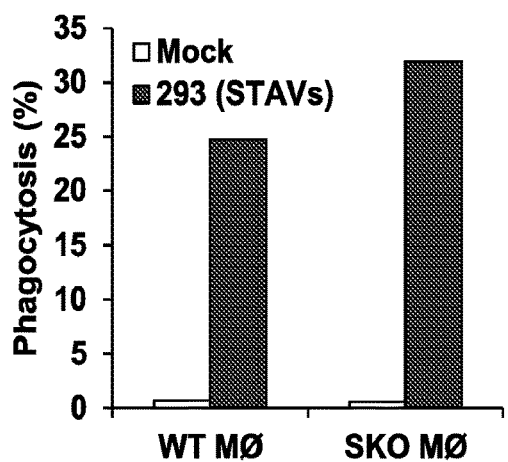
FIG. 4A-4D. Extrinsic STING signaling dependent gene expression in macrophages.
Figure 4C:
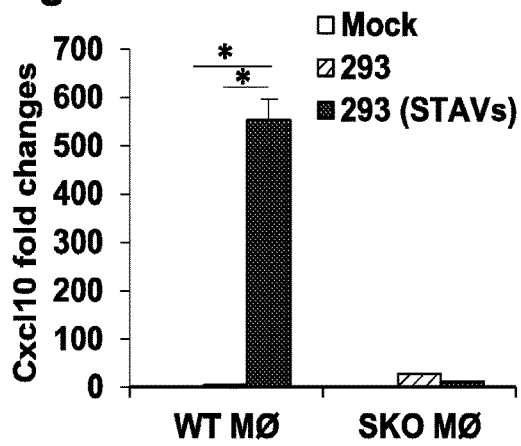
Figure 4D:
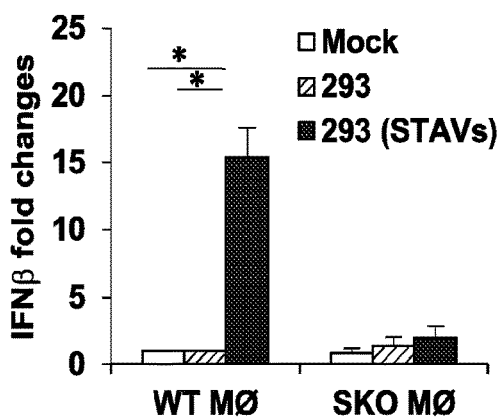
Figure 4B:

To evaluate the importance of STING signaling in the stimulation of APC's following cellular engulfment, B16 cells were transfected with STAVs, routinely obtaining greater than 90% transfection efficiency (FIG. 2A) and it was confirmed that B16 cells exhibited cytosolic DNA-dependent STING signaling as determined by observing an increase in cytokine production, including Cxcl10 (FIGS. 2B-E and FIG. 11). This was performed since it was previously noted that numerous types of cancer cells appear defective in STING signaling, perhaps to avoid DNA-damage mediated cytokine production that can occur via intrinsic STING signaling, which likely alerts the immune system to the vicinity of the damaged cell (Xia et al., Cell Rep 14:282-297, 2016; Xia et al., Cancer Res., 76:6747-6759, 2016). STAV containing cells were then UV treated, which triggered the apoptosis of greater than 90% within 24 hours, and the cells fed to phagocytes (murine bone marrow derived macrophages) in vitro (FIG. 2F), and 90% of the STAVs remained in the treated cells (FIG. 3A-B). Approximately 50% of the macrophages consistently engulfed the cells as determined using B16 cells transfected with fluorescently labeled STAVs (FIG. 2F-H, FIG. 3C). UV treated B16 cells alone or B16 cells containing Poly I:C failed to stimulate the macrophages as verified by measuring Cxcl10, type I IFN, macrophage maturation marker (CD86) and MHI class I (H2 kd) (FIG. 2I-L, FIG. 3D). However, B16 cells containing STAVs robustly induced the production of cytokines in macrophages that was dependent on extrinsic STING signaling within the macrophage (FIG. 2I-L). A similar effect was observed following the phagocytosis of HEK293 cells containing STAVs (FIG. 4 and FIG. 12). This data indicated that exogenous cytosolic DNA species present in engulfed apoptotic cells, but not apoptotic cells alone can potently stimulate the activation of macrophages in trans.

Figure 5A:
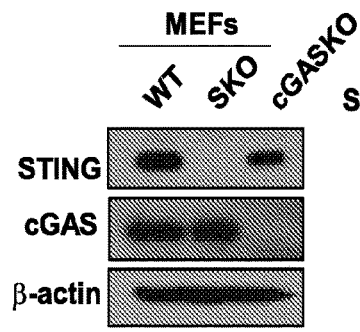
FIG. 5A-5H. Macrophage stimulation in trans by cytosolic DNA.
Figure 5C:
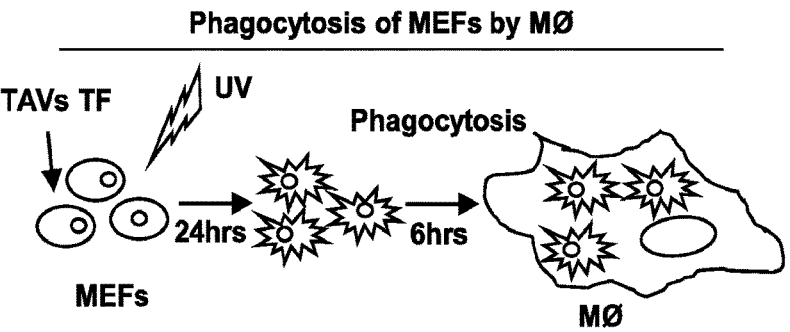
Figure 5B:
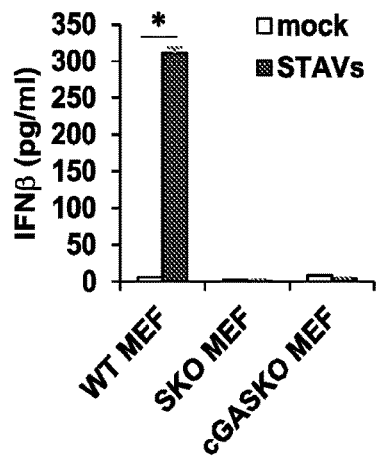
Figure 5D:
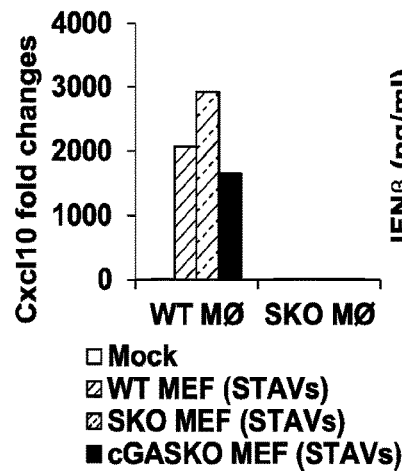
Figure 5E:
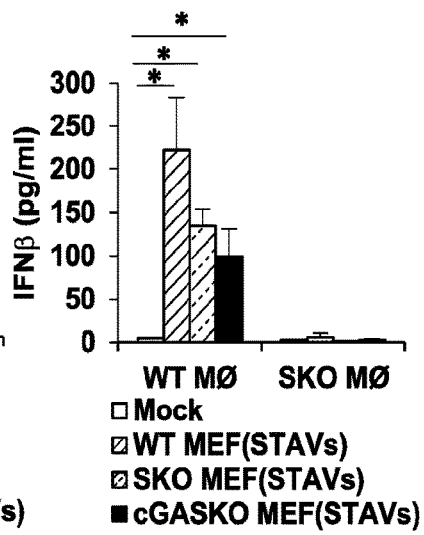
Figure 5F:
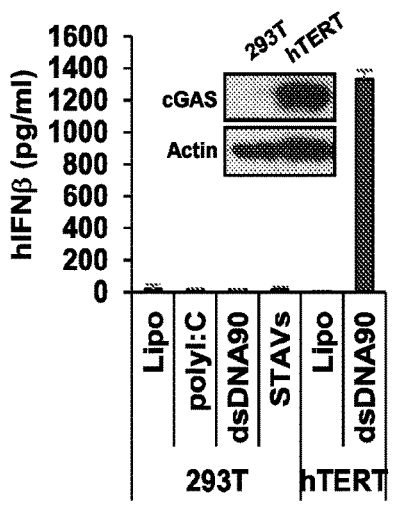
Figure 5G:
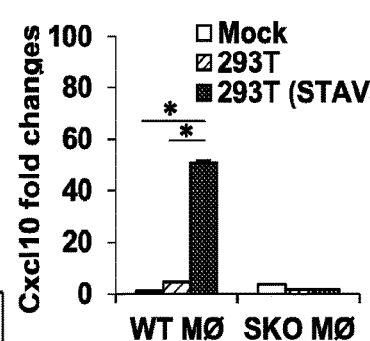
Figure 5H:
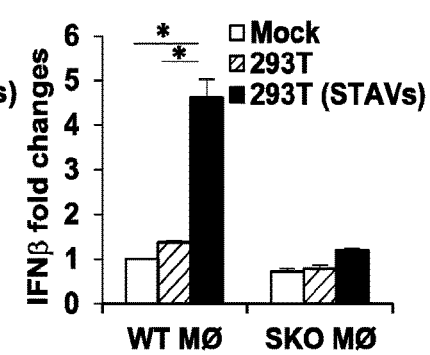

It is possible that the transfected cytosolic DNA could stimulate intrinsic STING signaling within the treated cell and facilitate the production of immunoregulatory cytokines that may provoke APC activation. To thus evaluate whether STING acts extrinsically or intrinsically within the engulfed cell itself, mouse embryonic fibroblasts (MEFs) that lacked STING or cGAS were treated with STAVs and confirmed that both STING and cGAS were required to produce cytokines such as type I IFN in the presence of cytosolic DNA (FIGS. 5A and 5B). UV treated MEFs were then incubated with macrophages to ascertain the latter's activation (FIG. 5C). The results again indicated that only apoptotic cells containing cytosolic DNA were able to activate macrophages (FIGS. 5D-5E). Indeed, MEFs lacking cGAS or STING, transfected with STAVs remained able to activate APCs, indicating that STING-dependent cytokine production within the engulfed cell was not completely essential for macrophage activation in vitro (FIGS. 5A, 5D, and 5E). This data suggests that exogenous cytosolic DNA but not endogenous cellular DNA, is responsible for the stimulation of the APCs including macrophages. To complement these studies STAVs were transfected into human 293T cells that lack both cGAS and STING. Unlike normal human hTERT cells, 293T cells are consequently unable to produce type I IFN in response to STAVs (FIG. 5F). STAVs-treated 293T cells were then incubated with murine macrophages and observed that only 293T cells containing STAVs were able to stimulate cytokine production in engulfing macrophages (FIG. 5G-5H). This effect was dependent on STING signaling in the macrophages (FIG. 5G-5H). Since neither cGAS nor STING are present within the 293T cell, the stimulation of engulfing macrophages can presumably directly occur in trans by cytosolic DNA (STAVs) promoting STING signaling in APCs (i.e., macrophages).

It is accepted in the field that the nuclear DNA, and plausibly mitochondrial DNA, undergoes degradation during the apoptotic process. The responsible nucleases within the nuclei include CAD (caspase activated DNAse), which cleaves the genomic DNA between nucleosomes (14, 19). Thus, fragments of nuclear DNA sufficient to activate STING may not be generated, nor escape into the cytosol to activate STING signaling.

In view of this, the importance of STING signaling for activation within in the engulfing APC, and the importance of extrinsic STING signaling, was examined. To accomplish this B16 cells were treated with STAVs and fed to murine macrophages lacking STING or cGAS. This analysis surprisingly indicted that macrophages lacking cGAS or TLR9, but not STING, were readily able to be activated by cells containing STAVs (FIG. 6A). Thus, STING, but not cGAS, is essential for the activation of APCs following cellular engulfment. This event did not require TLR9. However, cGAS itself was also not required for this process suggesting that STAVs within the UV treated cell could be binding to an alternate DNA binding, STING-activating molecule in the APCs or conversely that CDNs were being generated with the B16 cell by cGAS and these ligands are able to activate STING extrinsically within the APC, in trans. To evaluate this, it was confirmed that cGAS was expressed in B16 cells and mass spectrometry showed that STAV treated, but not untreated B16 cells, produced CDNs (FIG. 6B) and can likely also act in trans.

To further confirm this, 293T cells that lack cGAS or STING were transfected with STAVs. Unlike B16 or MEF cells, these cells cannot generate CDNs. It was confirmed that STAV-containing 293T cells were able to modestly stimulate control macrophages, but not macrophages that lacked STING (FIG. 6C). It was also observed that macrophages lacking cGAS were similarly unable to be activated by 293T cells containing STAVs, since the STAVs are probably unable to activate cGAS-generated CDNs production within the APC to activate STING (FIG. 6C). To explore this further, 293T cells were reconstituted with a plasmid expressing cGAS. Data shows that 293T cells expressing cGAS could readily generate CDN's, as determined by mass spectrometry and that these CDN containing cells could significantly activate macrophages in a STING-dependent manner, compared to cytosolic DNA (STAVs) alone (FIG. 6C). The cGAS re-constituted 293T cells could activate macrophages lacking cGAS itself, since the 293T generated CDNs could almost certainly act directly on STING (FIG. 6C-D). These effects were confirmed using a human colon cancer cell-line that similarly lacks cGAS (HT116) (FIG. 6E). In addition, the data indicated that the DNA virus HSV1 (γ34.5) also functioned similarly to the STAVs following infection of B16 cells. That is, only engulfed viral-infected cells and not uninfected cells, could activate macrophages. Further, this event occurred in a similar cGAS/STING-dependent manner (FIG. 6F).

The results suggest that STAVs transfected into cells can extrinsically activate the cGAS/STING axis in macrophages. Second, STAVs can generate CDNs within the treated cell which can also act in trans to stimulate extrinsic STING signaling in APCs. Further, reconstitution of cGAS, for example within a tumor cell, can generate CDNs which are able to similarly act in trans to stimulate the activation of macrophages via STING. Finally, host macrophages can distinguish between a viral infected and uninfected dying cell predominantly through cGAS/STING detection of viral cytoplasmic DNA, analogous to STAVs.

Given that CDNs generated within a cell exhibit considerable ability to stimulate macrophages in trans, CDNs were directly transfected into B16 and 293T cells and the cells fed to macrophages. This analysis indicated that tumor cells containing exogenously added CDN's were readily engulfed by macrophages, but were not potent activators of STING signaling in trans or of macrophage activation (FIG. 5). This is in contrast to when the cGAS was transfected within the tumor cell to generate endogenous CDNs. In contrast, the direct transfection of CDNs or indeed STAVs into APCs were readily able to induce their activation and to enhance the cross presentation of antigen in a STING specific manner (FIG. 7). The present results indicate that exogenously added CDN's do not appear to exert their anti-tumor effect by working on the cancer cell itself but more likely function by directly stimulating the APC to facilitate STING-dependent cytokine induced antigen cross-presentation following cellular engulfment.

The present data thus indicates that cytosolic DNA (STAVs) or CDNs can activate APCs directly or indirectly and facilitate antigen cross-presentation. It remained unclear why cytosolic DNA (STAVs) and not cellular DNA was able to stimulate APC's in trans. Nuclear DNA, and plausibly mitochondrial DNA, undergoes degradation during the apoptotic process. The responsible nucleases within the nuclei which cleaves genomic DNA between nucleosomes involves CAD (caspase activated DNAse) (14, 21). Thus, fragments of nuclear DNA sufficient to activate STING signaling may not be generated, nor escape into the cytosol. Following engulfment by macrophages, the remainder of the DNA is degraded by additional DNases such as DNaseII within the lysosomal compartment of APCs (13, 18). It is thus plausible that cytosolic DNA species (STAVs/viral DNA) escape cellular degradation within the apoptotic cell and following engulfment in APCs is more readily available the lysosomal compartment and stimulate extrinsic cGAS-STING signaling in the APC. To explore this further, macrophages from mice lacking DNase I (FIG. 8B), II (FIG.

Figure 8A:
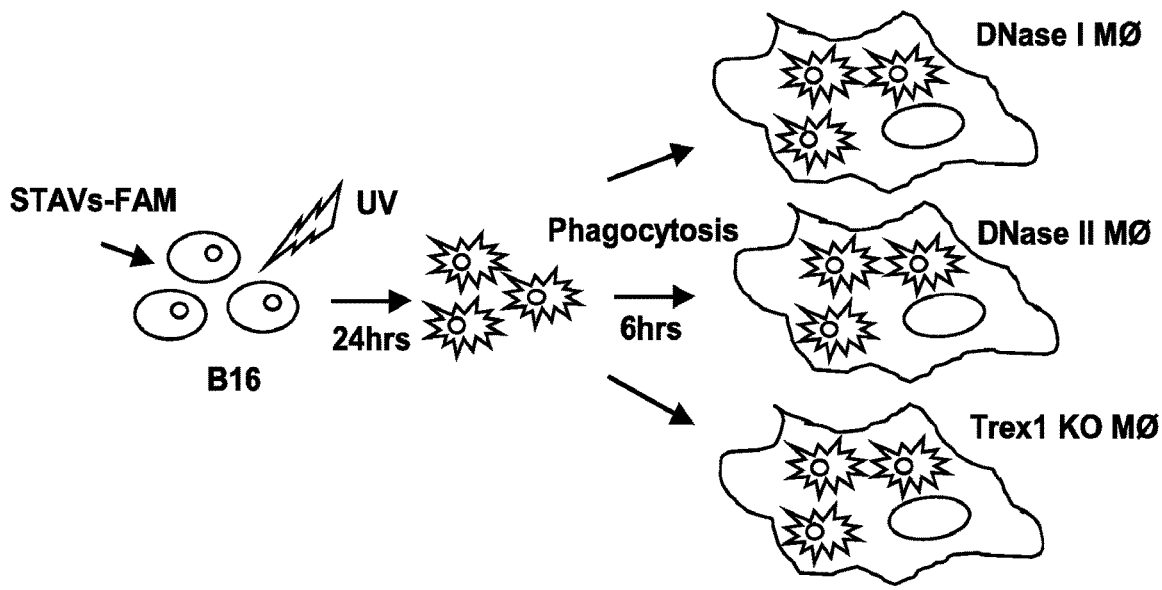
FIG. 8A-8D. Apoptotic cells containing STAVs escape degradation by DNase II.
Figures 8B, 8C, 8D:
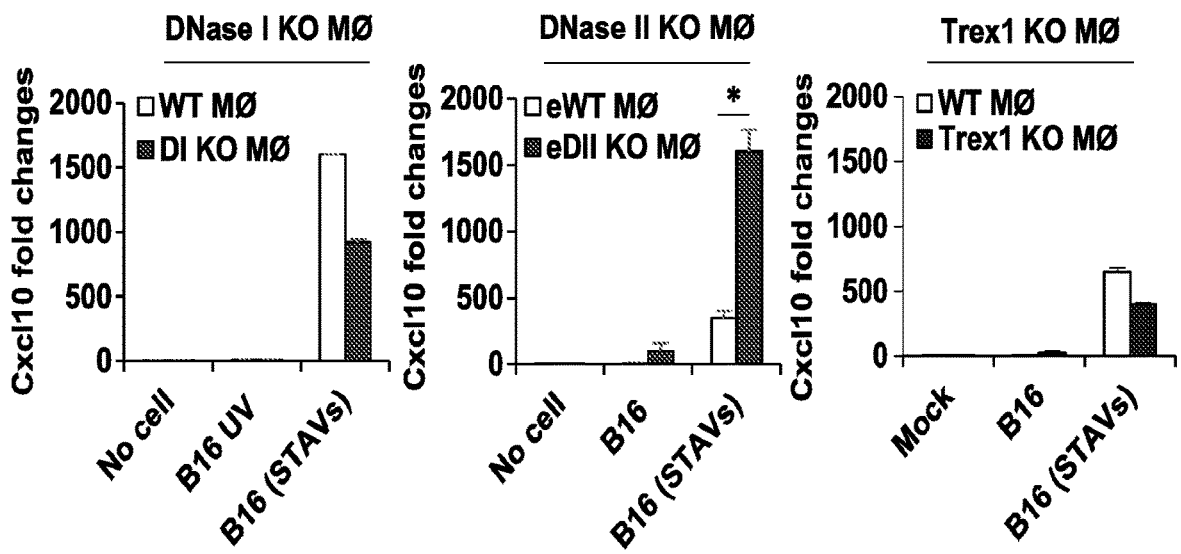

8B), or III (Trex1) (FIG. 8D) were retrieved and fed B16 cells containing or lacking STAVs. The data again indicated that apoptotic cells poorly activate normal macrophages, perhaps explaining why tumor cells are generally non-immunogenic. However, APCs lacking DNase II, but not DNase I or DNase III exhibited an increase in cytokine production following engulfment of untreated apoptotic cells (FIG. 8). This event was greatly augmented in STAVs containing cells (FIG. 8).

This data confirms that DNases such as CAD efficiently degrade self-DNA within apoptotic cells to help prevent the activation of macrophages. In addition, DNaseII in APC's predominantly ensures that any engulfed apoptotic DNA that escapes degradation is broken down in lysosomal compartments into non-STING activating nucleotides. Interestingly, cells containing cytosolic DNA (STAVs) or cytoplasmic viral DNA likely escape degradation in the dying cell and are able to stimulate extrinsic cGAS/STING signaling, prior to degradation of by DNaseII. Thus, CDN's as DAMPs may better avoid degradation following engulfment and enable a phagocyte to determined that the cell has been infected or undergone DNA damage, and become activated.

The data herein suggests that cells have devised efficient ways to eliminate the lethal possibility of self-DNA activating innate immune sensor pathways such as those governed by STING (18, 22). Likely, tumor cells also utilize this process to remain immunologically indolent. To determine whether STAVs could render tumor cells immunogenic in vivo, B16-OVA melanoma cells containing or lacking STAVs were intratumorally inoculated into immunocompetent C57BL/6J mice (FIG. 9A). It was observed that B16-OVA cells treated with STAVs exhibited less growth compared to mice inoculated with untreated cells (FIG. 9B). In addition, the STAVs containing cells did not exert any anti-tumor activity in the absence of STING in the recipient mice (FIG. 9C). The ability of the STAVs to inhibit tumor growth involved the generation of anti-tumor CTLs to the tumor, as determined by measuring anti-SIINFEKL specific CD8 T cells (FIG. 9D). This data would indicate that tumor cells containing STAVs could be potent stimulators of anti-tumor immunity.

To further evaluate whether STAV containing cells were able to generate immune responses in murine models, B16-OVA cells were loaded with STAVs and irradiated and used to immunize B6 mice (FIG. 10A). This study indicated that STAVs containing cells were competent to generate type II IFN, an indicator of CTL generation (FIG. 10B). STAV dependent type II IFN production was dependent on STING and cGAS, but not TLR9. This data would indicate that tumor cells containing STAVs could be potent stimulators of anti-tumor immunity. To examine this, C57BL/6 mice were inoculated intravenously with B16-OVA melanoma cells to include tumors and subsequently post-vaccinated with B16-OVA cells loaded with STAVs (FIG. 10C). Results showed that the B16 OVA tumors killed the majority of mice within 40 days (FIG. 10D). However, mice treated with B16-OVA STAVs had a median half-life of 70 days, with 40% of the mice alive after 100 days (FIG. 10D). Mice lacking STING (FIG. 10E) or cGAS (FIG. 10F), but not TLR9 (FIG. 10G), however, succumbed to lethal disease similar to wild type mice, indicating the importance of STING signaling in combatting cancer development. Thus, cells containing STAVs may provide an effective treatment for the prevention of cancer.

Collectively, the results indicate that cytosolic dsDNA species present within a dying cell can activate extrinsic STING signaling in phagocytes likely following association with cGAS which would generate CDNs. It is likely that the cytosolic DNA species avoid being degraded by nuclear DNAses, responsible for degrading genomic DNA. Such cytosolic species appear significantly more capable of activating STING in phagocytes, likely as a result of avoiding being degraded within the apoptotic cell. DNAse resistant cytosolic species were thus more competent at activating STING in trans. In addition, CDNs generated from an infected or damaged cell are able to directly activate STING-dependent signaling in APC's in trans to trigger inflammatory responses, the cross-presentation of antigen and the spontaneous generation of T cells. CDN's generated within a dying cell are also predominantly resistant to the activity of DNases within the engulfed phagocyte, unlike susceptible cellular DNA, which makes them highly efficient at stimulating extrinsic STING signaling. It is likely that tumorigenic cells closely mimic normal cells undergoing apoptosis and avoid triggering STING signaling. Thus, tumorigenic cells are predominantly non-immunogenic. It is hypothesized that intrinsic STING signaling is likely important within a dying/infected cell to alert APC's to the damaged region, while the extrinsic STING signaling component within macrophages is critical for the production of cytokines such as Type I interferon that facilitate cross presentation events.

The data indicates that numerous tumor cells exhibit defective STING signaling. This would presumably enable the damaged cell to avoid alerting the immune system for removal and for antigen presentation. However, the data also indicates that by suppressing pathogen or DNA damaged driven CDN generation, an engulfed cell would also avoid the activation of the APC itself. This may help explain why the STING/cGAS pathway is so commonly deregulated in certain cancers. The results further indicate that reconstitution of CDN's and STING signaling may not only alert the immune system to the damaged/infected/tumor cell, but also potently trigger cytokine production, inflammatory responses, antigen cross-presentation and spontaneous T cell generation. The use of STAVs to treat cancer, either directly into tumors, or carried inside tumor cells, or as vaccine adjuvants may provide powerful new anti-tumor therapies. Moreover, the generation of CDNs within a tumor cell may also provide a powerful approach to stimulate the anti-tumor T cell responses. Finally, the data provides an explanation for how phagocytes are able to avoid being activated following the engulfment of generally apoptotic cells versus a DNA damaged or infected cell, which contains DAMPs in the form of CDNs.

Numerous modifications and variations in the invention as set forth in the above illustrative examples are expected to occur to those skilled in the art. Consequently only such limitations as appear in the appended claims should be placed on the invention.

REFERENCES

1. Gajewski T F, Schreiber H, Fu Y X. Innate and adaptive immune cells in the tumor microenvironment. Nat Immunol. 2013; 14(10):1014-22.
2. Zitvogel L, Galluzzi L, Kepp O, Smyth M J, Kroemer G. Type I interferons in anticancer immunity. Nat Rev Immunol. 2015; 15(7):405-14.
3. Diamond M S, Kinder M, Matsushita H, Mashayekhi M, Dunn G P, Archambault J M, Lee H, Arthur C D, White J M, Kalinke U, Murphy K M, Schreiber R D. Type I interferon is selectively required by dendritic cells for immune rejection of tumors. J Exp Med. 2011; 208(10): 1989-2003.
4. Fuertes M B, Kacha A K, Kline J, Woo S R, Kranz D M, Murphy K M, Gajewski T F. Host type I IFN signals are required for antitumor CD8+ T cell responses through CD8{alpha}+dendritic cells. J Exp Med. 2011; 208(10): 2005-16.
5. Ma Y, Adjemian S, Mattarollo S R, Yamazaki T, Aymeric L, Yang H, Portela Catani J P, Hannani D, Duret H, Steegh K, Martins I, Schlemmer F, Michaud M, Kepp O, Sukkurwala A Q, Menger L, Vacchelli E, Droin N, Galluzzi L, Krzysiek R, Gordon S, Taylor P R, Van Endert P, Solary E, Smyth M J, Zitvogel L, Kroemer G. Anticancer chemotherapy-induced intratumoral recruitment and differentiation of antigen-presenting cells. Immunity. 2013; 38(4):729-41.
6. Marichal T, Ohata K, Bedoret D, Mesnil C, Sabatel C, Kobiyama K, Lekeux P, Coban C, Akira S, Ishii K J, Bureau F, Desmet C J. DNA released from dying host cells mediates aluminum adjuvant activity. Nat Med. 2011; 17(8):996-1002.
7. Barber G N. STING: infection, inflammation and cancer. Nat Rev Immunol. 2015; 15(12):760-70.
8. Woo S R, Fuertes M B, Corrales L, Spranger S, Furdyna M J, Leung M Y, Duggan R, Wang Y, Barber G N, Fitzgerald K A, Alegre M L, Gajewski T F. STING-dependent cytosolic DNA sensing mediates innate immune recognition of immunogenic tumors. Immunity. 2014; 41(5):830-42.
9. Corrales L, Glickman L H, McWhirter S M, Kanne D B, Sivick K E, Katibah G E, Woo S R, Lemmens E, Banda T, Leong J J, Metchette K, Dubensky T W, Jr., Gajewski T F. Direct Activation of STING in the Tumor Microenvironment Leads to Potent and Systemic Tumor Regression and Immunity. Cell Rep. 2015; 11(7):1018-30.
10. Deng L, Liang H, Xu M, Yang X, Burnette B, Arina A, Li X D, Mauceri H, Beckett M, Darga T, Huang X, Gajewski T F, Chen Z J, Fu Y X, Weichselbaum R R. STING-Dependent Cytosolic DNA Sensing Promotes Radiation-Induced Type I Interferon-Dependent Antitumor Immunity in Immunogenic Tumors. Immunity. 2014; 41(5):843-52.
11. Ablasser A, Goldeck M, Caviar T, Deimling T, Witte G, Rohl I, Hopfner K P, Ludwig J, Hornung V. cGAS produces a 2'-5'-linked cyclic dinucleotide second messenger that activates STING. Nature. 2013; 498(7454): 380-4.
12. Barber G N. STING-dependent cytosolic DNA sensing pathways. Trends Immunol. 2014; 35(2):88-93.
13. Kawane K, Fukuyama H, Kondoh G, Takeda J, Ohsawa Y, Uchiyama Y, Nagata S. Requirement of DNase II for definitive erythropoiesis in the mouse fetal liver. Science. 2001; 292(5521):1546-9.
14. Nagata S, Nagase H, Kawane K, Mukae N, Fukuyama H. Degradation of chromosomal DNA during apoptosis. Cell Death Differ. 2003; 10(1):108-16.
15. Ahn J, Barber G N. Self-DNA, STING-dependent signaling and the origins of autoinflammatory disease. Curr Opin Immunol. 2014; 31:121-6.
16. Belz G T, Smith C M, Eichner D, Shortman K, Karupiah G, Carbone F R, Heath W R. Cutting edge: conventional CD8 alpha+dendritic cells are generally involved in priming CTL immunity to viruses. J Immunol. 2004; 172(4): 1996-2000.
17. Smith C M, Belz G T, Wilson N S, Villadangos J A, Shortman K, Carbone F R, Heath W R. Cutting edge: conventional CD8 alpha+dendritic cells are preferentially involved in CTL priming after footpad infection with herpes simplex virus-1. J Immunol. 2003; 170(9):4437-40.
18. Ahn J, Gutman D, Saijo S, Barber G N. STING manifests self DNA-dependent inflammatory disease. Proc Natl Acad Sci USA. 2012; 109(47):19386-91.
19. McIlroy D, Tanaka M, Sakahira H, Fukuyama H, Suzuki M, Yamamura K, Ohsawa Y, Uchiyama Y, Nagata S. An auxiliary mode of apoptotic DNA fragmentation provided by phagocytes. Genes Dev. 2000; 14(5):549-58.

What is claimed:

1. A method of decreasing a size of a melanoma tumor in a subject in need thereof comprising administering intratumorally a composition comprising a STING (STimulator of INterferon Genes) activator comprising a double stranded DNA (dsDNA) comprising:
 a first strand comprising:
  between 70 nucleotides and 90 nucleotides with a modified 5' end comprising one or more phosphorothioate linkages, where the first strand comprises 80 percent or more of guanine nucleotides; and
 a second strand comprising:
  between 70 nucleotides and 90 nucleotides, where the second strand comprises 80 percent or more of cytosine nucleotides, where the STING activator induces STING signaling, where the melanoma tumor is decreased in size by between:
 a lower limit of 25%; and
 an upper limit of 50%.

2. A method of treating a cancer in a subject in need thereof comprising administering a composition comprising a STING (STimulator of INterferon Genes) activator comprising a double stranded DNA (dsDNA) having a modified 5' end comprising one or more phosphorothioate linkages and comprising between 70 and 90 nucleotides, where the STING activator induces STING signaling, where the STING activator induces Cxcl10 and/or type I IFN cytokine production to a melanoma tumor associated with the cancer thereby inhibiting the cancer.

3. The method of claim 2, where the cancer to be treated is selected from the group consisting of metastatic melanoma, malignant melanoma, recurrent melanoma of the skin, melanoma brain metastases, stage IIIA skin melanoma; stage IIIB skin melanoma, stage IIIC skin melanoma, stage IV skin melanoma, and malignant melanoma of head and neck.

4. The method of claim 2, where the melanoma tumor has a size in the subject, where the size is decreased by between:
 a lower limit of 25%; and
 an upper limit of 90%.

5. The method of claim 2, where a route of administration of the STING activator is selected from the group consisting of intratumorally, intravenously, intra-arterially, intraperitoneally, intranasally, intramuscularly, intradermally and subcutaneously.

6. The method of claim 2, where the STING activator induces infiltration of one or more antigen presenting cells into a melanoma tumor associated with the cancer.

7. The method of claim 6, where the one or more antigen presenting cells are macrophages or other phagocytes.

8. The method of claim 2, where the dsDNA is transfected into a cell, where the dsDNA remains cytosolic in the cell.

9. The method of claim 2, where the dsDNA is a mixture of eighty (80) percent or more of alternating A and T oligonucleotide residues or a mixture of eighty (80) percent or more of alternating G and C oligonucleotide residues.

10. The method of claim 2, further comprising a modified 3' end comprising one or more phosphorothioate linkages.

11. The method of claim 2, where the STING activator has a sequence as follows AAAAAAAAAAAAAAA-AAAAAAAAAAAAAAAAAAAAAAAAAAAAAAAAA-AAAAAA AAAAAAAAAAAAAAAAAAAAAAA-AAAAAAAAAAAA (SEQ ID NO: 1); or TTTTTTTTTTTTTTTTTTTTTTTTTTTTTTTTTTTTT-TTTTTTTTTTTTTTTTTTTTTTTT TTTTTTTTTTT-TTTTTTTTTTTTTTTT (SEQ ID NO: 2).

12. The method of claim 1, where the dsDNA is a mixture of eighty (80) percent or more of alternating A and T oligonucleotide residues or a mixture of eighty (80) percent or more of alternating G and C oligonucleotide residues.

13. The method of claim 1, further comprising a modified 3' end comprising one or more phosphorothioate linkages.

14. The method of claim 1, where the STING activator induces infiltration of one or more antigen presenting cells into the melanoma tumor.

15. The method of claim 14, where the one or more antigen presenting cells are macrophages or other phagocytes.

16. A method of decreasing a size of a melanoma tumor in a subject in need thereof comprising administering intratumorally a composition comprising a STING (STimulator of INterferon Genes) activator comprising:
 a double stranded DNA (dsDNA) comprising:
  a first strand comprising:
   a modified 5' end comprising one or more phosphorothioate linkages;
   a modified 3' end comprising one or more phosphorothioate linkages; and
   between: 70 nucleotides and 90 nucleotides, where the first strand comprises 80 percent or more of adenine nucleotides; and
  a second strand comprising:
   a modified 5' end comprising one or more phosphorothioate linkages;
   a modified 3' end comprising one or more phosphorothioate linkages; and
   between: 70 nucleotides and 90 nucleotides, where second strand comprises 80 percent or more of thymine nucleotides,
  where the melanoma tumor is decreased in size by between:
   a lower limit of 25%; and
   an upper limit of 90%.

17. The method of claim 16, where the STING activator induces infiltration of one or more antigen presenting cells into the melanoma tumor.

18. The method of claim 17, where the one or more antigen presenting cells are macrophages or other phagocytes.

19. The method of claim 16, where the first strand has a sequence as follows AAAAAAAAAAAAAA-AAAAAAAAAAAAAAAAAAAAAAAAAAAAAAAAA-AAAAAAA AAAAAAAAAAAAAAAAAAAAAAAA-AAAAAAAAAAAA (SEQ ID NO: 1).

20. The method of claim 19, where the second strand has a sequence as follows TTTTTTTTTTT- TTTTTTTTTTTTTTTTTTTTTTTTTTTTTTTTTTTTTTTTTTTTTTTTT TTTTTTTTTTTTTTTTTTTTTTTTTTTT (SEQ ID NO: 2).

21. The method of claim 16, further comprising where the STING activator is administered in vitro to the cancer cells, where the STING activator treated cancer cells are administered to the subject.

\* \* \* \* \*

```
SEQUENCE LISTING

<160> NUMBER OF SEQ ID NOS: 3

<210> SEQ ID NO 1
<211> LENGTH: 90
<212> TYPE: DNA
<213> ORGANISM: Artificial Sequence
<220> FEATURE:
<223> OTHER INFORMATION: Synthetic Polynucleotide

<400> SEQUENCE: 1
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa                                      90

<210> SEQ ID NO 2
<211> LENGTH: 90
<212> TYPE: DNA
<213> ORGANISM: Artificial Sequence
<220> FEATURE:
<223> OTHER INFORMATION: Synthetic Polynucleotide

<400> SEQUENCE: 2
tttttttttt tttttttttt tttttttttt tttttttttt tttttttttt tttttttttt      60
tttttttttt tttttttttt tttttttttt                                      90
```

<210> SEQ ID NO 3
<211> LENGTH: 379
<212> TYPE: PRT
<213> ORGANISM: Homo sapiens

<400> SEQUENCE: 3

```
Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp His Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365
```

```
Glu Lys Pro Leu Pro Leu Arg Thr Asp Phe Ser
    370                 375
```